(12) United States Patent
Günther et al.

(10) Patent No.: US 10,793,662 B2
(45) Date of Patent: Oct. 6, 2020

(54) NITROGEN-CONTAINING COMPOUNDS SUITABLE FOR USE IN THE PRODUCTION OF POLYURETHANES

(71) Applicant: Evonik Operations GmbH, Essen (DE)

(72) Inventors: Thomas Günther, Neuss (DE); Michael Fiedel, Essen (DE); Olga Fiedel, Essen (DE); Martin Glos, Borken (DE); Roland Hubel, Essen (DE)

(73) Assignee: Evonik Operations GmbH, Essen (DE)

( * ) Notice: Subject to any disclaimer, the term of this patent is extended or adjusted under 35 U.S.C. 154(b) by 272 days.

(21) Appl. No.: 15/323,154

(22) PCT Filed: Jul. 23, 2015

(86) PCT No.: PCT/EP2015/066827
§ 371 (c)(1),
(2) Date: Dec. 30, 2016

(87) PCT Pub. No.: WO2016/020199
PCT Pub. Date: Feb. 11, 2016

(65) Prior Publication Data
US 2018/0194889 A1    Jul. 12, 2018

(30) Foreign Application Priority Data

Aug. 5, 2014 (DE) ......................... 10 2014 215 382

(51) Int. Cl.
| | |
|---|---|
| *C08G 18/20* | (2006.01) |
| *C08G 18/66* | (2006.01) |
| *C08J 9/14* | (2006.01) |
| *C08G 18/18* | (2006.01) |
| *C08G 18/24* | (2006.01) |
| *C08G 18/76* | (2006.01) |
| *C08G 18/16* | (2006.01) |

(Continued)

(52) U.S. Cl.
CPC ....... *C08G 18/2018* (2013.01); *C07D 207/06* (2013.01); *C07D 403/12* (2013.01); *C07D 403/14* (2013.01); *C08G 18/165* (2013.01); *C08G 18/185* (2013.01); *C08G 18/1825* (2013.01); *C08G 18/1833* (2013.01); *C08G 18/1841* (2013.01); *C08G 18/1858* (2013.01); *C08G 18/2081* (2013.01); *C08G 18/244* (2013.01); *C08G 18/48* (2013.01); *C08G 18/4816* (2013.01); *C08G 18/4829* (2013.01); *C08G 18/6688* (2013.01); *C08G 18/7621* (2013.01); *C08G 18/7664* (2013.01); *C08G 18/7671* (2013.01); *C08J 9/141* (2013.01); *C08G 2101/0008* (2013.01); *C08G 2101/0016* (2013.01); *C08G 2101/0025* (2013.01); *C08G 2101/0041* (2013.01); *C08G 2101/0083* (2013.01); *C08G 2105/02* (2013.01); *C08G 2170/60* (2013.01); *C08G 2290/00* (2013.01); *C08G 2340/00* (2013.01); *C08G 2350/00* (2013.01); *C08G 2410/00* (2013.01); *C08J 2203/02* (2013.01); *C08J 2203/14* (2013.01); *C08J 2203/204* (2013.01); *C08J 2375/04* (2013.01)

(58) Field of Classification Search
CPC ............... C08G 18/2081; C08G 18/48; C08G 18/7671; C08G 18/4829; C08G 18/6688; C08G 18/7621; C08G 18/7664; C08G 18/165; C08G 18/4816; C08G 2101/0016; C08G 2101/0008; C08G 2101/0025; C08G 18/2018; C08G 18/185; C08G 18/244; C08G 18/1825; C08G 18/1841; C08G 18/1833; C08G 18/1858; C08G 2410/00; C08G 2350/00; C08G 2170/60; C08G 2101/0041; C08G 2340/00; C08G 2105/02; C08G 2290/00; C08G 2101/0083; C09J 9/141; C08J 2375/04; C08J 9/141; C08J 2203/14; C08J 2203/02; C08J 2203/204; C07D 207/06; C07D 403/12; C07D 403/14
See application file for complete search history.

(56) References Cited

U.S. PATENT DOCUMENTS

| 2,834,748 A | 5/1958 | Bailey et al. |
| 2,917,480 A | 12/1959 | Bailey et al. |

(Continued)

FOREIGN PATENT DOCUMENTS

| CA | 2008639 A1 | 8/1990 |
| CN | 102503909 A | 6/2012 |

(Continued)

OTHER PUBLICATIONS

German language Search Report dated Mar. 17, 2015 in DE 10 2014 215 382.4 (5 pages).

(Continued)

*Primary Examiner* — Rabon A Sergent
(74) *Attorney, Agent, or Firm* — Nexsen Pruet PLLC; Philip P. McCann

(57) ABSTRACT

The present invention provides for the use of nitrogen compounds of formula (I) and/or of corresponding quaternized and/or protonated compounds for production of polyurethanes, compositions containing these compounds and polyurethane systems, especially polyurethane foams, which have been obtained using the compounds.

13 Claims, No Drawings

(51) Int. Cl.
  *C08G 18/48* (2006.01)
  *C07D 207/06* (2006.01)
  *C07D 403/12* (2006.01)
  *C07D 403/14* (2006.01)
  *C08G 101/00* (2006.01)

(56) References Cited

U.S. PATENT DOCUMENTS

| | | | |
|---|---|---|---|
| 3,346,557 A | 10/1967 | Patton, Jr. et al. | |
| 3,629,308 A | 12/1971 | Bailey et al. | |
| 3,933,695 A | 1/1976 | Omietanski et al. | |
| 4,042,540 A | 8/1977 | Lammerting et al. | |
| 4,147,847 A | 4/1979 | Schweiger | |
| 4,379,861 A * | 4/1983 | Haas | C08G 18/2081 521/115 |
| 4,500,704 A | 2/1985 | Kruper, Jr. et al. | |
| 4,855,379 A | 8/1989 | Budnik et al. | |
| 5,134,217 A * | 7/1992 | Weider | C08G 18/2018 521/129 |
| 5,274,114 A * | 12/1993 | Weider | C07D 207/08 502/167 |
| 5,306,737 A | 4/1994 | Burkhart et al. | |
| 5,321,051 A | 6/1994 | Burkhart et al. | |
| 5,357,018 A | 10/1994 | Burkhart et al. | |
| 5,698,607 A * | 12/1997 | Heveling | C07D 295/02 521/129 |
| 6,355,763 B1 | 3/2002 | Scherzer et al. | |
| 6,359,022 B1 | 3/2002 | Hickey et al. | |
| RE38,415 E | 2/2004 | Weider et al. | |
| 6,762,274 B2 | 7/2004 | Waddington et al. | |
| 6,924,321 B2 | 8/2005 | Casati et al. | |
| 7,671,103 B2 | 3/2010 | Eilbracht et al. | |
| 7,671,104 B2 | 3/2010 | Heinemann et al. | |
| 7,838,566 B2 | 11/2010 | Glos et al. | |
| 7,858,829 B2 | 12/2010 | Hubei et al. | |
| 8,247,467 B2 | 8/2012 | Mijolovic et al. | |
| 8,303,843 B2 | 11/2012 | Glos et al. | |
| 8,334,355 B2 | 12/2012 | Henning et al. | |
| 8,349,907 B2 | 1/2013 | Henning et al. | |
| 8,609,798 B2 | 12/2013 | Knott et al. | |
| 8,623,984 B2 | 1/2014 | Henning et al. | |
| 8,729,207 B2 | 5/2014 | Hartung et al. | |
| 8,735,458 B2 | 5/2014 | Glos et al. | |
| 8,802,744 B2 | 8/2014 | Knott et al. | |
| 8,841,403 B2 | 9/2014 | Schmitz et al. | |
| 8,906,974 B2 | 12/2014 | Glos et al. | |
| 8,912,277 B2 | 12/2014 | Glos | |
| 8,921,437 B2 | 12/2014 | Knott et al. | |
| 8,946,310 B2 | 2/2015 | Glos et al. | |
| 8,957,121 B2 | 2/2015 | Schiller et al. | |
| 8,969,502 B2 | 3/2015 | Knott et al. | |
| 9,051,424 B2 | 6/2015 | Lobert et al. | |
| 9,056,952 B2 | 6/2015 | Eilbracht et al. | |
| 9,096,706 B2 | 8/2015 | Schmitz et al. | |
| 9,217,074 B2 | 12/2015 | Glos et al. | |
| 9,328,210 B2 | 5/2016 | Terheiden et al. | |
| 9,346,919 B2 | 5/2016 | Jazkewitsch et al. | |
| 9,353,225 B2 | 5/2016 | Knott et al. | |
| 9,481,695 B2 | 11/2016 | Knott et al. | |
| 9,988,483 B2 * | 6/2018 | Forkner | C08G 18/4829 |
| 2002/0103091 A1 | 8/2002 | Kodali | |
| 2006/0167125 A1 | 7/2006 | Bauer et al. | |
| 2006/0229375 A1 | 10/2006 | Hsiao et al. | |
| 2006/0293400 A1 | 12/2006 | Wiltz, Jr. et al. | |
| 2007/0072951 A1 | 3/2007 | Bender et al. | |
| 2007/0238800 A1 | 10/2007 | Neal et al. | |
| 2007/0270518 A1 | 11/2007 | Nutzel | |
| 2007/0282026 A1 | 12/2007 | Grigsby, Jr. et al. | |
| 2008/0114105 A1 | 5/2008 | Hell et al. | |
| 2008/0234402 A1 | 9/2008 | Lehmann et al. | |
| 2009/0088488 A1 | 4/2009 | Bruckner et al. | |
| 2009/0088489 A1 | 4/2009 | Terheiden et al. | |
| 2010/0029587 A1 | 2/2010 | Brueckner et al. | |
| 2010/0036011 A1 | 2/2010 | De Gans et al. | |
| 2010/0240786 A1 | 9/2010 | Glos et al. | |
| 2011/0062370 A1 | 3/2011 | Eilbracht et al. | |
| 2011/0257280 A1 | 10/2011 | Glos et al. | |
| 2011/0306694 A1 | 12/2011 | Glos et al. | |
| 2012/0037036 A1 | 2/2012 | Veit et al. | |
| 2012/0153210 A1 | 6/2012 | Glos et al. | |
| 2012/0190760 A1 | 7/2012 | Henning et al. | |
| 2012/0190762 A1 | 7/2012 | Hubei et al. | |
| 2012/0264843 A1 | 10/2012 | Glos | |
| 2013/0035407 A1 | 2/2013 | Lobert et al. | |
| 2013/0035409 A1 | 2/2013 | Hubei et al. | |
| 2013/0068990 A1 | 3/2013 | Eilbracht et al. | |
| 2013/0150472 A1 | 6/2013 | Hubei et al. | |
| 2013/0213267 A1 | 8/2013 | Fiedel et al. | |
| 2013/0217930 A1 | 8/2013 | Haensel et al. | |
| 2014/0058004 A1 | 2/2014 | Schmitz et al. | |
| 2015/0031781 A1 | 1/2015 | Landers et al. | |
| 2015/0057384 A1 | 2/2015 | Glos et al. | |
| 2015/0158968 A1 | 6/2015 | Schmitz et al. | |
| 2015/0368420 A1 | 12/2015 | Schmitz et al. | |
| 2016/0046757 A1 | 2/2016 | Landers et al. | |
| 2016/0075846 A1 | 3/2016 | Krebs et al. | |
| 2016/0096939 A1 | 4/2016 | Glos et al. | |
| 2016/0152739 A1 | 6/2016 | Eilbracht et al. | |
| 2016/0161001 A1 | 6/2016 | Jobe et al. | |
| 2016/0208050 A1 | 7/2016 | Klotzbach et al. | |
| 2016/0264711 A1 | 9/2016 | Krebs et al. | |
| 2016/0264757 A1 | 9/2016 | Krebs et al. | |
| 2016/0304666 A1 | 10/2016 | Emmrich-Smolczyk et al. | |
| 2016/0304685 A1 | 10/2016 | Emmrich-Smolczyk et al. | |
| 2016/0311961 A1 | 10/2016 | Klostermann et al. | |
| 2016/0326330 A1 | 11/2016 | Schuette et al. | |

FOREIGN PATENT DOCUMENTS

| | | |
|---|---|---|
| DE | 701825 C | 1/1941 |
| DE | 2439278 A1 | 2/1976 |
| DE | 2533074 A1 | 3/1976 |
| DE | 4229402 A1 | 3/1994 |
| DE | 4239054 A1 | 5/1994 |
| DE | 102004001408 A1 | 7/2005 |
| DE | 102007046860 A1 | 4/2009 |
| EP | 0054219 A1 | 6/1982 |
| EP | 0380993 A2 | 8/1990 |
| EP | 0493836 A1 | 7/1992 |
| EP | 0495249 A1 | 7/1992 |
| EP | 0527427 A2 | 2/1993 |
| EP | 533202 A1 | 3/1993 |
| EP | 0780414 A2 | 6/1997 |
| EP | 0839852 A2 | 5/1998 |
| EP | 0656382 B1 | 8/1998 |
| EP | 867465 A1 | 9/1998 |
| EP | 0872505 A1 | 10/1998 |
| EP | 1161474 A1 | 12/2001 |
| EP | 1537159 A1 | 6/2005 |
| EP | 1544235 A1 | 6/2005 |
| EP | 1678232 A2 | 7/2006 |
| EP | 1712578 A1 | 10/2006 |
| EP | 1977825 A1 | 10/2008 |
| EP | 1985642 A1 | 10/2008 |
| EP | 1985644 A1 | 10/2008 |
| EP | 2042534 A1 | 4/2009 |
| EP | 2104696 B1 | 9/2013 |
| SU | 1421738 A1 | 9/1988 |
| WO | 9612759 A2 | 5/1996 |
| WO | 0047647 A1 | 8/2000 |
| WO | 0058383 A1 | 10/2000 |
| WO | 0158976 A1 | 8/2001 |
| WO | 0222702 A1 | 3/2002 |
| WO | 03029320 A1 | 4/2003 |
| WO | 2004020497 A1 | 3/2004 |
| WO | 2004060956 A1 | 7/2004 |
| WO | 2004096882 A1 | 11/2004 |
| WO | 2005033167 A2 | 4/2005 |
| WO | 2005063841 A1 | 7/2005 |
| WO | 2005085310 A2 | 9/2005 |
| WO | 2005111109 A1 | 11/2005 |
| WO | 2005118668 A1 | 12/2005 |
| WO | 2006055396 A1 | 5/2006 |
| WO | 2006094227 A2 | 9/2006 |

(56) References Cited

FOREIGN PATENT DOCUMENTS

| WO | 2006116456 A1 | 11/2006 |
|---|---|---|
| WO | 20070111828 A2 | 10/2007 |
| WO | 2008058913 A1 | 5/2008 |
| WO | 2009058367 A1 | 5/2009 |
| WO | 2009130470 A1 | 10/2009 |
| WO | 2010028362 A1 | 3/2010 |
| WO | 2011163133 A1 | 12/2011 |
| WO | 2012072441 A1 | 6/2012 |
| WO | 2013019462 A1 | 2/2013 |
| WO | 2013022932 A1 | 2/2013 |
| WO | 2013102053 A1 | 7/2013 |

OTHER PUBLICATIONS

German language Written Opinion dated Jan. 18, 2016 in PCT/EP2015/066827 (13 pages).
Gunther et al., U.S. Appl. No. 15/322,275, filed Dec. 27, 2016.
Gunther et al., U.S. Appl. No. 15/322,514, filed Dec. 28, 2016.
Gunther et al., U.S. Appl. No. 15/404,324, filed Jan. 12, 2017.
International Search Report dated Jan. 18, 2016 in PCT/EP2015/066827 (3 pages).
Wing-Leung et al., "A green catalysis of CO2 fixation to aliphatic cyclic carbonates by a new ionic liquid system," Applied Catalysis A: General, Elsevier Science, Amsterdam, NL, vol. 472, Dec. 2013, pp. 160-166.
Wing-Leung et al., "Controlling the selectivity of the manganese/bicarbonate/hydrogen peroxide catalytic system by a biphasic pyrrolidinium ionic liquid/n-heptane medium," Applied Catalysis A: General, Elsevier Science, Amsterdam, NL, vol. 453, Jan. 2013, pp. 244-249.

* cited by examiner

NITROGEN-CONTAINING COMPOUNDS SUITABLE FOR USE IN THE PRODUCTION OF POLYURETHANES

This application is a national stage application under 35 U.S.C. § 371 of International Application No. PCT/EP2015/066827 filed 23 Jul. 2015, which claims priority to German Application No. 102014215382.4 filed 5 Aug. 2014, the disclosures of which are expressly incorporated herein by reference.

FIELD

The present invention lies in the field of nitrogen compounds, especially of amines, and of polyisocyanate polyaddition products, especially of polyurethanes. More particularly, it relates to the use of nitrogen compounds of the formula (I) and correspondingly quaternized and/or protonated compounds for production of polyurethanes, especially of polyurethane foams, to compositions containing these compounds and to polyurethane systems which have been obtained using the compounds.

BACKGROUND

The use of tertiary amines in the production of polyurethanes is known. A multitude of structurally different amines are used here as catalysts.

Polyurethanes are understood here to mean all reaction products proceeding from isocyanates, especially from polyisocyanates, and correspondingly isocyanate-reactive molecules. These include polyisocyanurates, polyureas, and allophanate-, biuret-, uretdione-, uretonimine- or carbodiimide-containing isocyanate or polyisocyanate reaction products. Preference is given to the use of the tertiary amines in the production of polyisocyanate polyaddition products.

Polyurethane systems are, for example, polyurethane coatings, polyurethane adhesives, polyurethane sealants, polyurethane elastomers or polyurethane foams, also referred to as PU foams.

Particularly in the case of production of polyurethane foams, tertiary amines play an important role, since what is called the blowing reaction—water reacts with isocyanate to form carbon dioxide as blowing gas—and the gel reaction—polyols react with isocyanates to give urethanes, which leads to a rise in the molar mass and corresponding gelation—have to be matched exactly to one another here, in order that a high-quality foam can form.

Polyurethane foams are cellular and/or microcellular polyurethane materials and can be divided roughly into closed-cell or partly closed-cell rigid polyurethane foams and open-cell or partly open-cell flexible polyurethane foams. Rigid polyurethane foams are used predominantly as insulation materials, for example in refrigerator systems or in the thermal insulation of buildings. Flexible polyurethane foams are used in a multitude of technical applications in industry and the domestic sector, for example for sound deadening, for production of mattresses or for cushioning of furniture. A particularly important market for various types of PU foams, such as conventional flexible foams based on ether or ester polyols, cold-cure flexible foams, also referred to as cold-cure foams hereinafter (frequently also as "high-resilience" (HR) foams), and rigid foams, and also foams having properties between these two classifications, is the automobile industry. It is possible here, for example, to use rigid foams as inner roof liner, ester foams as interior door trim and for die-cut sun visors, and cold-cure and flexible foams for seat systems and mattresses.

With regard to flexible foams, a distinction can also be made between cold-cure flexible foams and hot-cure flexible foams, as described, for example, in EP 2042534 A1, to which reference is made here in full.

SUMMARY

There is a continuing need for further alternative catalysts, preferably nitrogen catalysts, especially alternative amines, suitable for production of polyurethanes and polyurethane foams, preferably suitable for production of low-odor, ageing-resistant polyurethane systems having low amine emissions or other emissions, for example formaldehyde and/or dimethylformamide (DMF).

The specific problem addressed by the present invention was therefore that of providing an alternative catalyst for production of polyisocyanate reaction products, preferably polyurethanes, especially polyurethane foams, which preferably have low odor, are ageing-resistant and/or are free of emissions or at worst are afflicted by low amine emissions or other emissions, for example formaldehyde and/or dimethylformamide (DMF).

It has been found that, surprisingly, this problem is solved by compounds of the formula (I) below and the correspondingly quaternized and/or protonated compounds, i.e. said problem is solved by the use of the compounds of the formula (I) and by the use of the corresponding protonated compounds and by the use of the corresponding quaternized compounds and also by use of corresponding mixtures.

DETAILED DESCRIPTION

The present invention therefore provides for the use of at least one nitrogen compound or a corresponding quaternized and/or protonated compound in the production of polyisocyanate polyaddition products, preferably of polyurethanes, especially of polyurethane foams, wherein this nitrogen compound satisfies the formula (I)

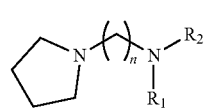

with n=1-30, especially 2-12, preferably 2-6, more preferably 2-3, especially preferably 2, where $R_1$ is H or a linear, branched or cyclic, aliphatic or aromatic, saturated or unsaturated hydrocarbyl radical which is optionally substituted by one or more heteroatoms or interrupted by one or more heteroatoms and has 1-30 carbon atoms, where $R_2$ is a linear, branched or cyclic, aliphatic or aromatic, saturated or unsaturated hydrocarbyl radical which is optionally substituted by one or more heteroatoms or interrupted by one or more heteroatoms and has 1-30 carbon atoms.

The expression "use of at least one nitrogen compound or of a corresponding quaternized and/or protonated compound", in the context of this invention, here and hereinafter, encompasses the use of the nitrogen compound in question and also the use of the corresponding protonated compounds and also the use of the corresponding quaternized compounds and also the use of corresponding mixtures.

The nitrogen compounds of the formula (I) used in accordance with the invention and correspondingly quaternized and/or protonated compounds, and also mixtures of the above, are suitable as catalysts for production of polyisocyanate reaction products, preferably of polyurethanes, especially of polyurethane foams, and can catalyze either the gel reaction or the blowing reaction in the foaming, and also advantageously further isocyanate reactions as described hereinafter.

Advantageously, the present invention additionally enables reduction or avoidance of catalysis-related emissions in the production of polyurethane systems, especially of polyurethane foams.

More particularly, it is an additional advantage of the invention that the nitrogen compounds of the formula (I) used in accordance with the invention or correspondingly quaternized and/or protonated compounds, and also mixtures of the above, advantageously have low emissions, and are preferably free of typically unwanted emissions from the resulting polyurethane systems, especially polyurethane foams, more preferably flexible polyurethane foams, advantageously in that they have low emissions with respect to emissions of nitrogen compounds, also called amine emissions hereinafter, advantageously low emissions with respect to emissions of dimethylformamide (DMF), and advantageously low emissions with respect to aldehyde emissions, especially with respect to formaldehyde emissions.

The scope of "low emissions" with respect to amines in the context of the present invention is especially such that the polyurethane system, preferably the polyurethane foam, further preferably the flexible polyurethane foam, more preferably the hot-cure flexible polyurethane foam, preferably for production of mattresses and/or furniture cushions, has an amine emission of $\geq 0$ µg/m$^3$ and $\leq 40$ µg/m$^3$, preferably $\leq 10$ µg/m$^3$, more preferably $\leq 5$ µg/m$^3$, appropriately determined by the test chamber method based on DIN standard DIN EN ISO 16000-9:2008-04, 24 hours after test chamber loading, and/or that the polyurethane system, preferably the polyurethane foam, especially the flexible polyurethane foam, more preferably the cold-cure flexible polyurethane foam, preferably for production of polyurethanes for use in the automobile industry, especially in automobile interiors, for example as inner roof liner, interior door trim, die-cut sun visors, steering wheels and/or seat systems, has an amine emission also referred to hereinafter as VOC emission or VOC value to VDA 278 (VOC=Volatile Organic Compounds) of $\geq 0$ µg/g and $\leq 40$ µg/g, preferably $\leq 10$ µg/g, more preferably $\leq 5$ µg/g, in accordance with the VDA 278 analysis method in the version dated October 2011, "Thermodesorptionsanalyse organischer Emissionen zur Charakterisierung nichtmetallischer KFZ-Werkstoffe" [Thermal desorption analysis of organic emissions for characterization of nonmetallic automobile materials] (30 minutes at 90° C.), and/or that the polyurethane system, especially the flexible polyurethane foam, more preferably the cold-cure flexible polyurethane foam, preferably for production of polyurethanes for use in the automobile industry, especially in automobile interiors, for example as inner roof liner, interior door trim, die-cut sun visors, steering wheels and/or seat systems, has an amine emission also called fog emission or fog value to VDA 278 hereinafter (fog: nonvolatile substances which condense readily at room temperature and contribute to fogging of the windscreen) of $\geq 0$ µg/g and $\leq 40$ µg/g, preferably $\leq 10$ µg/g, more preferably $\leq 5$ µg/g, in accordance with the VDA 278 analysis method in the version dated October 2011 (60 minutes at 120° C.). VDA is the German Association of the Automotive Industry (www.vda.de). According to the field of use of the polyurethane systems, especially of the polyurethane foams, for example in the case of use in the automobile industry, there may be limits according to the vehicle manufacturer specification for total emissions of volatile organic compounds (VOC$_{tot}$ and/or Fog$_{tot}$), for example VOC$_{tot} \leq 100$ µg/g and/or Fog$_{tot} \leq 250$ µg/g. It is all the more important that the contribution of amines to the total emissions (VOC$_{amine}$ and/or Fog$_{amine}$) is at a minimum. The determination methods chosen in the context of the present invention, based on DIN standard DIN EN ISO 16000-9:2008-04 and VDA 278, are elucidated in detail in the examples section.

"Low emissions" with respect to emissions of dimethylformamide (DMF) in the context of the present invention means especially that the inventive nitrogen compounds of the formula (I), (II), (III), (IV), (V), (VI), (VII) and/or (VIII) and/or corresponding polyurethane systems, preferably polyurethane foams, especially flexible polyurethane foams, more preferably hot-cure flexible polyurethane foams, produced using the aforementioned compounds, have DMF emissions of $\geq 0$ ppm and $\leq 5$ ppm, preferably $\leq 1$ ppm, more preferably $\leq 0.1$ ppm. Advantageously, the present invention thus enables especially the provision of flexible polyurethane foams, very particularly hot-cure flexible polyurethane foams having particularly low emissions with respect to emissions of dimethylformamide. In the context of the present invention, "DMF emission" is not a subset of "amine emission".

"Low emissions" with respect to emissions of aldehydes, especially of formaldehyde, in the context of the present invention means especially that the polyurethane system, preferably the polyurethane foam, especially the flexible polyurethane foam, meets the limits for aldehyde emissions, especially for formaldehyde emissions, fixed by foam manufacturers and the furniture industry in Europe and the USA within the scope of the voluntary "CertiPUR" programme, and/or that the exchange of the conventional catalysts, especially of amines, particularly of tertiary amines containing one or more N-methyl or N,N-dimethyl groups according to the prior art, for nitrogen compounds for use in accordance with the invention leads to an improvement in the aldehyde-related, especially formaldehyde-related, emissions in the formulation of a corresponding polyurethane system. The limit for formaldehyde emissions according to "CertiPUR", for example for mattresses, is 0.1 mg/m$^3$, measured to ASTM method D5116-97 "Small Chamber Test", with conditioning for 16 hours. A person skilled in the art is aware of different analytical methods for determining aldehyde emissions. VDA 275, VDA 277 or else VDA 278 may be cited by way of example, as well as various chamber test methods. VDA is the German Association of the Automotive Industry (www.vda.de). "VDA 275", in the version dated July 1994, gives a test method for determination of aldehyde release, especially of formaldehyde release, by the modified bottle method, wherein the derivatization reagent for aldehydes used may, as well as the customarily used acetylacetone (via photometric detection), also be 2,4-dinitrophenylhydrazine (2,4-DNP) (detection via HPLC after external calibration), in order to be able to better detect not only formaldehyde but also acetaldehyde and propionaldehyde. In the context of this invention, reference is made to both method designs of this VDA 275 as preferred methods for determining aldehyde emissions, especially formaldehyde emissions.

Advantageously, the present invention thus enables the provision of polyurethane systems, preferably of polyurethane foams, especially of flexible polyurethane foams, having particularly low emissions with respect to emissions of nitrogen compounds, also called amine emissions hereinafter, even given different demands, and preferably being free of such emissions.

Advantageously, the present invention thus enables the provision of polyurethane systems, preferably of polyurethane foams, especially of flexible polyurethane foams, produced using the aforementioned nitrogen compounds, having particularly low emissions with respect to emissions of dimethylformamide (DMF), even given different demands, and preferably being free of such emissions.

Advantageously, the present invention contributes to provision of polyurethane systems, preferably polyurethane foams, especially of flexible polyurethane foams, produced using the aforementioned nitrogen compounds, having lower emissions with respect to emissions of aldehydes, especially of formaldehyde, even given different demands, than corresponding nitrogen-containing catalysts or corresponding polyurethane systems in which conventional catalysts, especially tertiary amines containing one or more N-methyl or N,N-dimethyl groups according to the prior art, are used in place of the inventive nitrogen compounds. This is because standard amines or PU systems containing standard amines can otherwise contain formaldehyde as an impurity, for example because of the industrial production thereof, for example because formaldehyde or methanol was used as alkylating agent in the amine production.

Advantageously, the present invention also contributes to the provision of low-odor polyurethane systems, preferably polyurethane foams, especially of flexible polyurethane foams. "Low-odor" means here that the resulting polyurethane system has a minimum level of product odor, especially when the inventive nitrogen compounds are used as alternative catalysts to catalysts according to the prior art, which can be tested especially by olfactory testing by a panel of trained olfactory testers.

Advantageously, the present invention also contributes to an improvement in the ageing characteristics, especially to the heat resistance and/or ageing resistance when heated (thermal ageing), of polyurethane systems, preferably polyurethane foams, especially flexible polyurethane foams. Such ageing phenomena are often closely related to the choice of catalyst system for production of the polyurethane systems, and generally lead to material fatigue. With the inventive nitrogen compounds, it is possible here in an advantageous manner to improve the heat stability and/or service life of the corresponding polyurethane systems compared to polyurethane systems which have been produced with conventional catalysts according to the prior art. Advantageously, this effect can be observed especially in the case of polyurethane foams, preferably flexible slabstock foams, especially in the context of dry heat ageing according to DIN standard DIN EN ISO 2440/A1:2009-01, especially at a temperature of 70, 100, 120, 125 and/or 140° C. and with an ageing time of 2, 4, 16, 22, 24, 48, 72 and/or 168 hours, preferably for 2, 24 and/or 168 hours, when inventive nitrogen compounds of the formula (I) are used in the foaming as alternatives to structurally related catalysts according to the prior art.

Advantageously, the present invention also enables the provision of preferably discoloration-minimized polyurethane systems, especially polyurethane foams, preferably polyurethanes for use in the automobile industry, especially in automobile interiors, for example as inner roof liners, interior door trim, die-cut sun visors, steering wheels and/or seat systems, where the polyurethane systems provided using inventive nitrogen-containing catalysts especially lead to lower discoloration of plastics, especially plastic covers, in automobile interiors than those polyurethane systems which can be produced using conventional catalysts according to the prior art, especially noninventive amines. This can be shown by a PVC discoloration test according to the Volkswagen test method VW PV 3937, amine emissions by the indicator method.

Advantageously, the present invention enables more processing latitude in the production of polyurethane systems, especially of semirigid polyurethane foams (open-cell rigid foams, for example for use as inner roof lining in automobile interiors). This means that, in an advantageous manner, greater variation in the use concentration of the inventive nitrogen compounds is possible without any adverse effect on the desired material properties, for example the open-cell content of the foam or the three-dimensional weight distribution over the foam block, compared to comparable amine catalysts, or those typically used for such applications, according to the prior art. This means an enormous simplification of user operations.

For possible quaternization of the compounds of the formula (I), it is possible to use any reagents known as quaternizing reagents. Preferably, quaternizing agents used are alkylating agents, for example dimethyl sulphate, methyl chloride or benzyl chloride, preferably methylating agents such as dimethyl sulphate in particular. Quaternization is likewise possible with alkylene oxides, for example ethylene oxide, propylene oxide or butylene oxide, preferably with subsequent neutralization with inorganic or organic acids.

The compounds of the formula (I), if quaternized, may be singly or multiply quaternized. Preferably, the compounds of the formula (I) are only singly quaternized. In the case of single quaternization, the compounds of the formula (I) are preferably quaternized on one nitrogen atom which is part of a ring, preferably a pyrrolidine ring.

The compounds of the formula (I) can be converted to the corresponding protonated compounds by reaction with organic or inorganic acids. These protonated compounds may be preferred, for example, when, for example, a slowed polyurethane reaction is to be achieved, or when the reaction mixture on application is to have improved flow characteristics.

Organic acids used may, for example, be all the abovementioned organic acids, for example carboxylic acids having 1 to 36 carbon atoms (aromatic or aliphatic, linear or branched), for example formic acid, lactic acid, 2-ethylhexanoic acid, salicylic acid and neodecanoic acid, or else polymeric acids, for example polyacrylic or polymethacrylic acids. Inorganic acids used may, for example, be phosphorus-based acids, sulphur-based acids or boron-based acids.

However, the use of compounds of the formula (I) which have not been quaternized or protonated is particularly preferred in the context of this invention.

The subject-matter of the invention is described hereinafter by way of example, without any intention of limiting the invention to these illustrative embodiments. Where ranges, general formulae or classes of compounds are indicated in what follows, they shall encompass not just the corresponding ranges or groups of compounds that are explicitly mentioned, but also all sub-ranges and sub-groups of compounds which are obtainable by extraction of individual values (ranges) or compounds. When documents are cited in the context of the present description, the contents thereof, particularly with regard to the subject-matter that forms the context in which the document has been cited, are considered in their entirety to form part of the disclosure-content of the present invention. Unless stated otherwise, percentages are figures in percent by weight. When mean values are reported hereinafter, the values in question are weight averages, unless stated otherwise. When parameters which have been determined by measurement are reported hereinafter, they have been determined at a temperature of 25° C. and a pressure of 101 325 Pa, unless stated otherwise.

Polyurethane (PU) in the context of the present invention is especially understood to mean a product obtainable by reaction of polyisocyanates and polyols, or compounds having isocyanate-reactive groups. As well as the polyurethane, it is also possible to form further functional groups, for example uretdiones, carbodiimides, isocyanurates, allophanates, biurets, ureas and/or uretonimines. Therefore, PU is understood in the context of the present invention to mean both polyurethane and polyisocyanurate, polyureas, and polyisocyanate reaction products containing uretdione, carbodiimide, allophanate, biuret and uretonimine groups. In the context of the present invention, polyurethane foam (PU foam) is understood to mean foam which is obtained as reaction product based on polyisocyanates and polyols or compounds having isocyanate-reactive groups. As well as the groups which give polyurethane its name, it is also possible to form further functional groups, for example allophanates, biurets, ureas, carbodiimides, uretdiones, isocyanurates or uretonimines. For the purposes of the present invention, the term PU foams therefore refer both to polyurethane foams (PUR foams) and polyisocyanurate foams (PIR foams). Preferred polyurethane foams are flexible polyurethane foams, rigid polyurethane foams and integral polyurethane foams. Particular preference is given in this context to conventional flexible polyurethane foams based on ether or ester polyols, highly elastic cold-cure polyurethane foams (frequently also referred to as "high-resilience" (HR) foams), viscoelastic polyurethane foams, semirigid polyurethane foams and rigid polyurethane foams, and also foams which have properties between these classifications and are used in the automobile industry.

In a preferred embodiment of the invention, at least one nitrogen compound of the formula (I) is used, with
$R_1$=H and

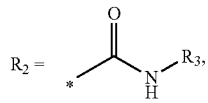

and so at least one nitrogen compound of the formula (I) which satisfies the formula (II) is used (II)

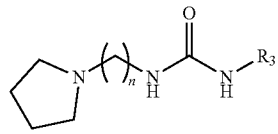

with n=2-12, especially 2-6, preferably 2 or 3, especially preferably 3,
where $R_3$=H or a linear, branched or cyclic, aliphatic or aromatic, saturated or unsaturated hydrocarbyl radical which is optionally substituted by one or more heteroatoms or interrupted by one or more heteroatoms and has 1 to 30 carbon atoms, preferably selected from the following radicals:

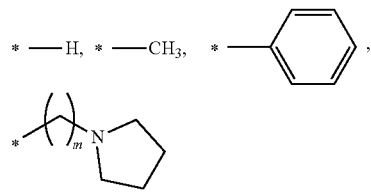

with m=3-6, preferably 3,
and where this nitrogen compound is especially selected from the group comprising

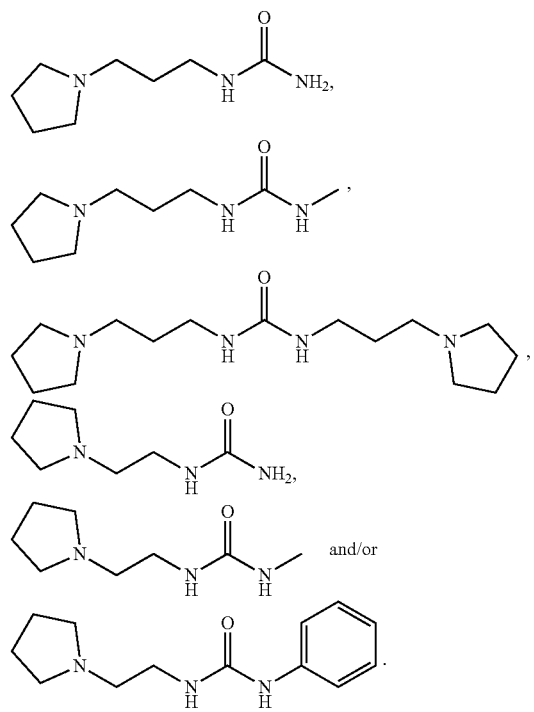

In a further preferred embodiment of the invention, at least one nitrogen compound of the formula (I) is employed, with
$R_1$=H and

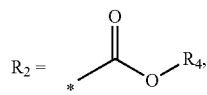

and so at least one nitrogen compound of the formula (I) which satisfies the formula (III) is used (III)

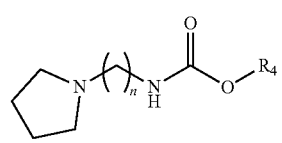

with n=2-12, especially 2-6, preferably 2 or 3, especially preferably 3, where $R_4$=a linear, branched or cyclic, aliphatic or aromatic, saturated or unsaturated hydrocarbyl radical which is optionally substituted by one or more heteroatoms or interrupted by one or more heteroatoms and has 1 to 30 carbon atoms, preferably selected from the following radicals:

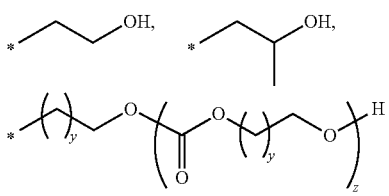

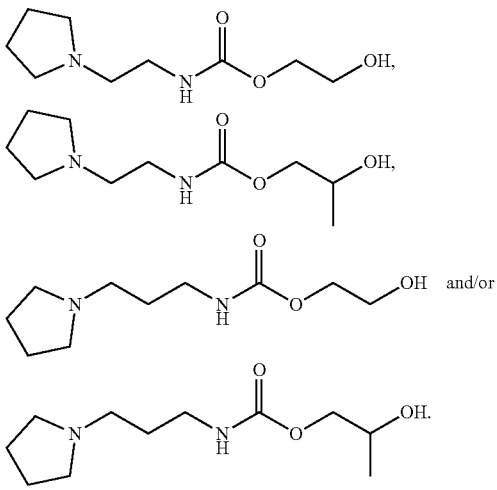

with y=1-10, preferably 2-6, and z=1-100, especially 1-30, preferably 1-12, more preferably 1-6,
and where this nitrogen compound is especially selected from the group comprising

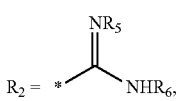

In yet a further preferred embodiment of the invention, at least one nitrogen compound of the formula (I) is employed, with
$R_1$=H and

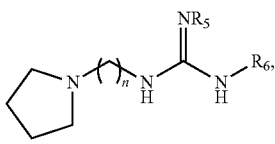

and so at least one nitrogen compound of the formula (I) which satisfies the formula (IV) is used (IV)

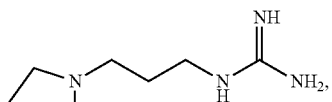

with n=2-12, especially 2-6, preferably 2 or 3, especially preferably 3,
where $R_5$, $R_6$ are the same or different and are each H or a linear, branched or cyclic, aliphatic or aromatic, saturated or unsaturated hydrocarbyl radical which is optionally substituted by one or more heteroatoms or interrupted by one or more heteroatoms and has 1 to 30 carbon atoms,
preferably selected from the following radicals:

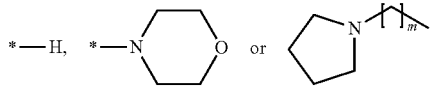

with m=2-6, preferably 2-3, more preferably 3,
and where this nitrogen compound is especially selected from the group comprising

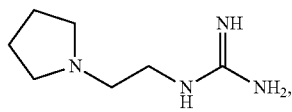

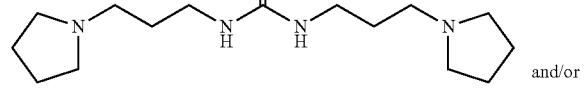

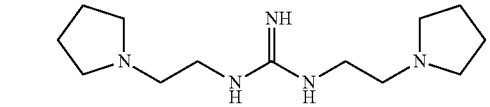 and/or

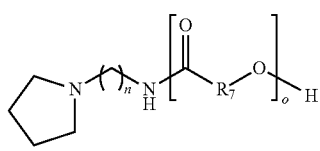

In a further preferred embodiment of the invention, at least one nitrogen compound of the formula (I) is employed, with
$R_1$=H and

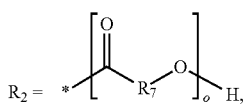

and so at least one nitrogen compound of the formula (I) which satisfies the formula (V) is used (V)

with n=2-12, especially 2-6, preferably 2 or 3, especially preferably 3,
and o=1-100, especially 1-30, preferably 1-12, more preferably 1-6,
where $R_7$=a linear, branched or cyclic, aliphatic or aromatic, saturated or unsaturated hydrocarbyl radical which is optionally substituted by one or more heteroatoms or interrupted by one or more heteroatoms and has 1 to 30 carbon atoms.

In yet a further preferred embodiment of the invention, at least one nitrogen compound of the formula (I) is employed, where R₁ and R₂ are bridged to form a pyrrolidine cycle, and so at least one nitrogen compound of the formula (I) which satisfies the formula (VI) is used,

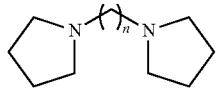
(VI)

with n=2-12 except for 4, preferably 2, 3 or 6, more preferably 6, and where this nitrogen compound is especially selected from

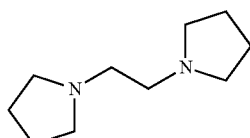

and/or

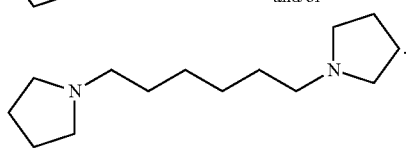

In a further preferred embodiment of the invention, at least one nitrogen compound of the formula (I) is employed, where R₁ and R₂ are bridged to form a piperazine cycle, and so at least one nitrogen compound of the formula (I) which satisfies the formula (VII) is used,

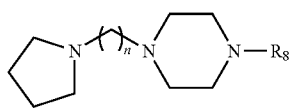
(VII)

with n=2-12, especially 2-6, preferably 2 or 3, especially preferably 3, and R₈=H or a linear, branched or cyclic, aliphatic or aromatic, saturated or unsaturated hydrocarbyl radical which is optionally substituted by one or more heteroatoms or interrupted by one or more heteroatoms and has 1 to 30 carbon atoms, preferably selected from the following radicals:

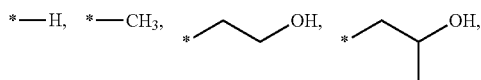

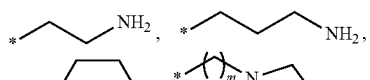

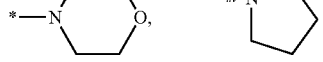

with 2-6, preferably 2-3, more preferably 3, and where this nitrogen compound is especially selected from the group comprising

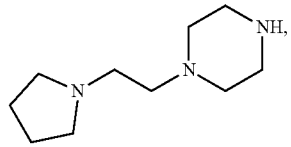

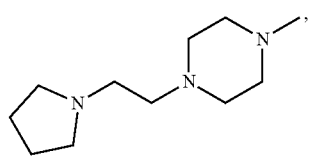

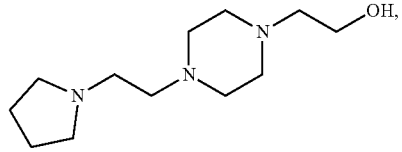

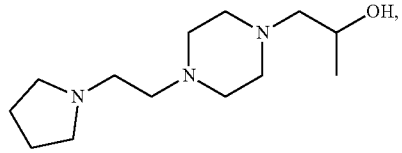

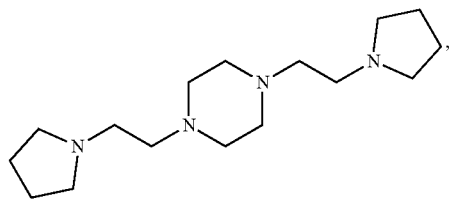

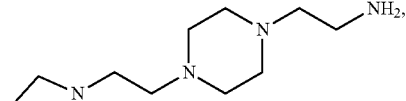

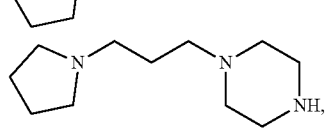

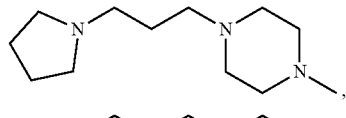

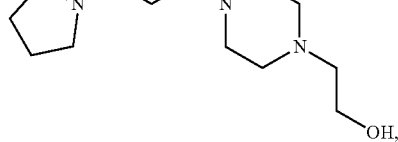

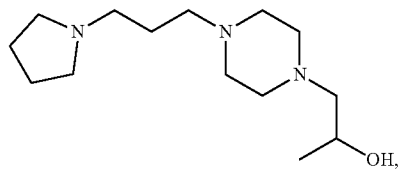

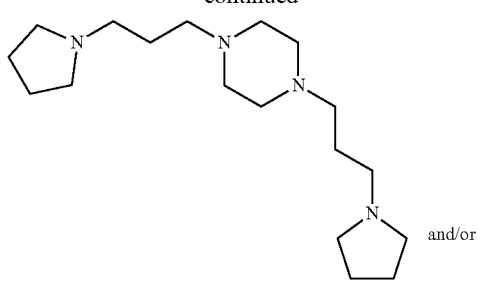

and/or

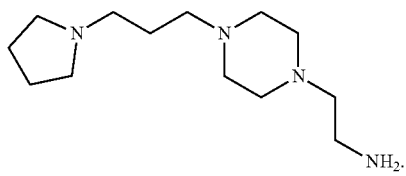

In a further preferred embodiment of the invention, at least one nitrogen compound of the formula (I) is employed, where R$_1$ and R$_2$ are bridged to form a triazine cycle, and so at least one nitrogen compound of the formula (I) which satisfies the formula (VIII) is used,

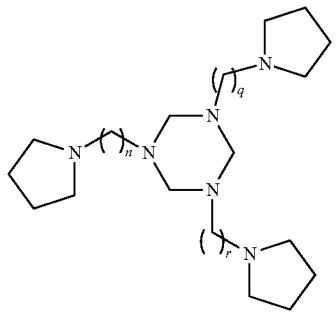
(VIII)

with identical or different n, q, r=2-12, especially 2-6, preferably 2 or 3, especially preferably 3, and where this nitrogen compound is especially

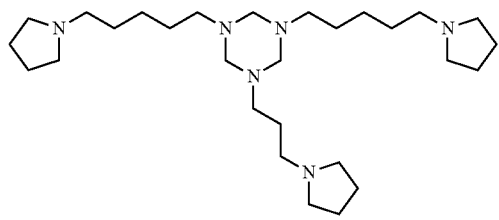

and/or

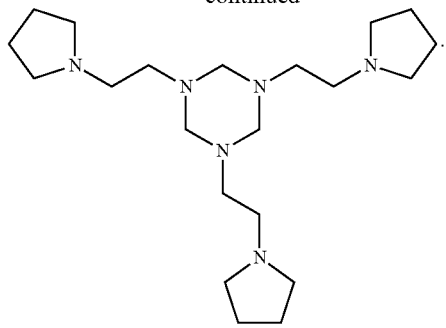

In a further preferred embodiment of the invention, at least one nitrogen compound of the formula (I) is employed,
with n=2-12, especially 2-6, preferably 2 or 3, especially preferably 3,
and R$_1$, R$_2$ are the same or different and are each H or

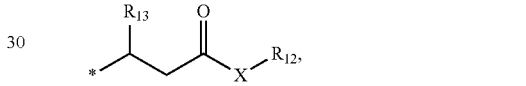

with the proviso that R$_1$ and R$_2$ are not both H, with
t, u independently=1-20,
s=1-36,
X═O or NH,
where R$_9$ is H or a linear, branched or cyclic, aliphatic or aromatic, saturated or unsaturated hydrocarbyl radical which is optionally substituted by one or more heteroatoms or interrupted by one or more heteroatoms, preferably has ester functions, urethane functions or amide functions, and has 1 to 30 and preferably 1 to 22, carbon atoms, and is more preferably hydrogen,
where R$_{10}$, R$_{11}$ are the same or different and are each a linear, branched or cyclic, aliphatic or aromatic, saturated or unsaturated hydrocarbyl radical having 1 to 30 and preferably 1 to 22 carbon atoms,
where R$_{12}$ is H or a linear, branched or cyclic, aliphatic or aromatic, saturated or unsaturated hydrocarbyl radical which is optionally substituted by one or more heteroatoms or interrupted by one or more heteroatoms and has 1 to 30 and preferably 1 to 22 carbon atoms,
where R$_{13}$ is H or a radical of the formula (X):

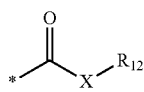
(X)

with X and R$_{12}$ as defined above.

If, in the context of this invention, at least one nitrogen compound of the formula (I), (II), (III), (IV), (V), (VI), (VII) and/or (VIII) is mentioned, this encompasses the use of a plurality of different nitrogen compounds of the formulae (I), (II), (III), (IV), (V), (VI), (VII) and/or (VIII), for example the joint use of nitrogen compounds of the formulae (III) and (IV), and the use of the corresponding protonated compounds, and also the use of the corresponding quaternized compounds, and also the use of corresponding mixtures of all the aforementioned nitrogen compounds of the formulae (I), (II), (III), (IV), (V), (VI), (VII) and/or (VIII), or corresponding protonated and/or quaternized compounds.

The above-described inventive nitrogen compounds of the formula (I), (II), (III), (IV), (V), (VI), (VII) and/or (VIII) are obtainable in principle via standard methods for amine preparation. A good overview of the preparation and derivatization of amines, for example with ethylene oxide and propylene oxide (alkoxylation), for preparation of ureas, especially also of the synthesis of pyrrolidine, is described in the article "Amines, Aliphatic" in Ullmann's Encyclopedia of Industrial Chemistry, Wiley-VCH, Weinheim, 2012, Vol. 2, p. 647-698 (DOI: 10.1002/14356007.a02_001) and the references present therein.

Preferred synthesis units, in the context of the present invention, are especially polyols, preferably diols, for example glycols, amines, polyamines, especially diamines, or amino alcohols, and also alkyl chlorides bearing amino groups, especially those aforementioned synthesis units which already have a pyrrolidine function. Polyols used with preference are, for example, monoethylene glycol (MEG), 1,2-propylene glycol (PG), butane-1,4-diol or hexane-1,6-diol. Polyamines used with preference are, for example, linear or branched, aliphatic diamines each having two terminal primary amino groups, for example butane-1,4-diamine or hexane-1,6-diamine, preferably ethylenediamine (EDA), trimethylenediamine, 1-(2-aminoethyl)pyrrolidine or 1-(3-aminopropyl)pyrrolidine, which can be obtained, for example, in accordance with the process described in WO 2012072441 or as described by Krupka and Jiri et al. in Czechoslovak Chemical Communications, 65 (11), 1805-1819; 2000, by a cyanoethylation and reduction to the amine, or as described in SU1421738 (A1) or by Katritzky et al. in Journal of Organic Chemistry (1994), 59, 5206-5214. The synthesis of 1-(3-aminopropyl)pyrrolidine is additionally described in the examples section. Amino alcohols used with preference can be obtained, for example, by reaction of ammonia or amines with epoxides (alkoxylation), preferably with ethylene oxide (EO) and/or propylene oxide (PO), by reaction of alcohols or polyols, preferably of diols, especially of glycols, with acrylonitrile (Michael reaction) and subsequent hydrogenation, as described, for example, in Catalysis Today, 1998, 44, 277-283, and/or by amination of alcohols or polyols, preferably of diols, especially of glycols, with ammonia or amines by known methods, as described, for example, by Beller et al. in Chem. Asian J. 2007, 2, 403-410, by Milstein et al. in Angew. Chem. 2008, 120, 8789-8792, by Watson and Williams in Science 2010, vol. 329, p. 635-636 or by Borner et al. in Chem Cat Chem 2010, 2, 640-643. Examples of these are monoethanolamine (MEA), 3-amino-1-propanol, 1-(2-hydroxyethyl)pyrrolidine and 1-(3-hydroxypropyl)pyrrolidine. The polyamines, polyols and amino alcohols described here in exact terms are all commercially available. Alkyl chlorides bearing amino groups can be obtained, for example, by reaction of bischloroalkyl compounds, for example 1,2-dichloroethane, 1,4-dichlorobutane or 1,6-dichlorohexane, with one equivalent of an amine, especially with pyrrolidine (nucleophilic substitution). Inventive ureas and guanidines can be obtained, for example, by reaction of the corresponding primary amines with urea, methylurea or guanidine hydrochloride. Triazines can be prepared by reaction of primary amines with formaldehyde, described, for example, in EP 0872505 or DE 2439278. The inventive urethane-functionalized compounds of the formula (III) can be prepared, for example, by reaction of the corresponding amines with carbonates such as propylene carbonate or ethylene carbonate.

The pyrrolidine groups present in all the compounds can be introduced here either at the start or at the end, according to the desired synthesis route. It may be preferable here to use pyrrolidine itself, for example in the case of reaction of pyrrolidine with alkyl halides, especially with alkyl chlorides (nucleophilic substitution), as described, for example, by Aitken et al. in Tetrahedron, 2002, vol. 58, 29, p. 5933-5940 or by Tijskens et al. in Journal of Organic Chemistry, 1995, vol. 60, 26, p. 8371-8374, and/or by reaction of pyrrolidine with bischloroalkyl ethers, and/or by reaction of pyrrolidine with epoxides (alkoxylation) or epoxide-bearing compounds, especially with ethylene oxide (EO) and/or propylene oxide (PO), as described, for example, by Reppe et al. in Justus Liebigs Annalen der Chemie, 1955, vol. 596, p. 1149 or by Moffett et al. in Journal of Organic Chemistry, 1949, vol. 14, p. 862-866 and in Org. Synth. Coll., 1963, vol. IV, p. 834ff, and/or by reaction of pyrrolidine with alcohols and/or polyols, preferably diols, especially glycols, for example in a transition metal-catalyzed execution as described by Jenner et al. in Journal of Organometallic Chemistry, 373 (1989), 343-352. In addition, the pyrrolidine function can also be introduced by reaction of butane-1,4-diol, as again described, for example, by Jenner et al. in Journal of Organometallic Chemistry, 373 (1989), 343-352, and/or by reaction of butane-1,4-diol with ammonia and organic compounds bearing hydroxyl groups, preferably of polyols, especially diols, preferably of glycols such as monoethylene glycol (MEG) or diethylene glycol (DEG) and/or amino alcohols, especially containing a primary hydroxyl function, as described, for example, in DE 701825C. For illustration, the preparation and performance testing of selected inventive compounds of the formula (I) is described in detail in the examples section.

Reagents used to obtain compounds of the formula (I) with

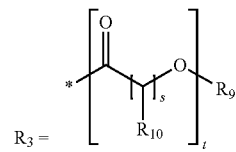

$R_3 =$ may, for example, be hydroxycarboxylic acids or lactones, for example hydroxystearic acid, lactic acid, butyrolactone or valerolactone.

Reagents used to obtain compounds of the formula (I) or (II) with

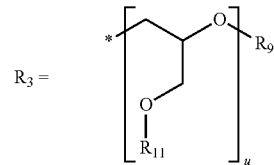

$R_3 =$ may, for example, be glycidol or glycidyl ether.

Reagents used to obtain compounds of the formula (I) or (II) with

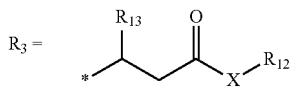

may, for example, be maleic acid derivatives, (meth) acrylic acid derivatives or acrylamide.

The preparation of some compounds of the formula (II), (III), (IV), (V) and (VI) that are particularly preferred in accordance with the invention is described, inter alia, in the examples section.

According to the preparation process, a nitrogen compound of the formula (I), especially of the formula (II), (III), (IV), (V), (VI), (VII) and/or (VIII), according to the quality of the process chosen and the number of corresponding purification steps, may be in technical quality, also referred to hereinafter as technical product mixtures, i.e. may include, for example, intermediates and/or by-products as secondary constituents and/or further impurities. The use of technical product mixtures is also a preferred embodiment in the context of this invention.

A preferred embodiment of the invention is especially the inventive use wherein at least one nitrogen compound of the formula (I), preferably at least one nitrogen compound of the formula (II), (III), (IV), (V), (VI), (VII) and/or (VIII), more preferably at least one nitrogen compound of the formula (II) and/or (VI), is used as a technical product mixture, especially comprising impurities, intermediates and/or by-products as further constituents, especially comprising pyrrolidine, 1-(3-aminopropyl)pyrrolidine, 1-(2-aminoethyl) pyrrolidine, 1-(2-hydroxyethyl)pyrrolidine, 1-(3-hydroxypropyl)pyrrolidine, trimethylenediamine, ethylenediamine (EDA), butane-1,4-diol, monoethylene glycol (MEG), diethylene glycol (DEG) and/or monoethanolamine (MEA), in a total amount of up to 95% by weight, preferably ≤70% by weight, especially ≤30% by weight, preferably ≤10% by weight, more preferably ≤5% by weight. A lower limit may be, for example, ≥0% by weight or, for example, 0.1% by weight.

A preferred embodiment of the invention is especially the inventive use of a technical product mixture, wherein the technical product mixture comprises (a) at least one nitrogen compound of the formula (I), especially at least one nitrogen compound of the formula (II), (III), (IV), (V), (VI), (VII) and/or (VIII), more preferably at least one nitrogen compound of the formula (II) and/or (VI), advantageously in a total amount of ≥5% by weight, preferably 20%-95% by weight, especially 30%-70% by weight, (b) optionally 1-(3-aminopropyl)pyrrolidine, advantageously in an amount of ≥5% by weight, preferably 20%-95% by weight, especially 30%-70% by weight, (c) optionally 1-(2-aminoethyl)pyrrolidine, advantageously in an amount of ≥5% by weight, preferably 20%-95% by weight, especially 30%-70% by weight, (d) optionally 1-(2-hydroxyethyl)pyrrolidine, advantageously in an amount of ≥5% by weight, preferably 20%-95% by weight, especially 30%-70% by weight, (e) optionally 1-(3-hydroxypropyl)pyrrolidine, advantageously in an amount of ≥5% by weight, preferably 20%-95% by weight, especially 30%-70% by weight, (f) optionally trimethylenediamine, advantageously in an amount of ≥5% by weight, especially 20%-95% by weight, preferably 30%-70% by weight, (g) optionally ethylenediamine (EDA), advantageously in an amount of ≤95% by weight, especially 20%-90% by weight, preferably 30%-80% by weight, (h) optionally butane-1,4-diol, advantageously in an amount of ≤95% by weight, especially 20%-90% by weight, preferably 30%-80% by weight, (i) optionally monoethylene glycol (MEG), advantageously in an amount of ≤95% by weight, especially 20%-90% by weight, preferably 30%-80% by weight, (j) optionally diethylene glycol (DEG), advantageously in an amount of ≤95% by weight, especially 20%-90% by weight, preferably 30%-80% by weight, and/or (k) optionally monoethanolamine (MEA), advantageously in an amount of ≤95% by weight, especially 20%-90% by weight, preferably 30%-80% by weight.

In the context of the aforementioned preferred embodiment, particularly preferred technical product mixtures in the context of the present invention are those compositions in which at least one nitrogen compound of the formula (I), (II), (III), (IV), (V), (VI), (VII) and/or (VIII) and/or a corresponding quaternized and/or protonated compound is used in combination with b), with c), with d), with e), with f), with g), with h), with i), with j), with k), with b) and h), with c) and h), with d) and h), with e) and h), with b) and i), with c) and i), with d) and i), with e) and i), with b) and j), with c) and j), with d) and j), with e) and j), with b) and d), with b), d) and h), with b), d) and i) or with b), d) and j).

Preferably, the above-described compounds of the formula (I), (II), (III), (IV), (V), (VI), (VII) and/or (VIII) and/or corresponding quaternized and/or protonated compounds are used in the inventive production of polyurethane systems, preferably for production of polyurethane coatings, polyurethane adhesives, polyurethane sealants, and polyurethane elastomers or especially for production of polyurethane foams as catalysts. The compounds of the formula (I) and/or the corresponding quaternized and/or protonated compounds can be used here in addition to standard catalysts or as a substitute for standard catalysts. More particularly, the inventive compounds can be used as a substitute for other nitrogen-containing catalysts, also referred to hereinafter as amine catalysts or amines, and, according to the application, as a partial or full substitute for standard metallic catalysts according to the prior art.

Therefore, in a preferred embodiment of the invention, at least one nitrogen compound of the formula (I), (II), (III), (IV), (V), (VI), (VII) and/or (VIII), a correspondingly quaternized and/or protonated compound, or mixtures of the nitrogen compound of the formula (I), (II), (III), (IV), (V), (VI), (VII) and/or (VIII) with corresponding quaternized and/or protonated compounds, is used as catalyst in the production of polyurethane systems, especially polyurethane foams. More particularly, said nitrogen compound can also be used as a technical product mixture. Suitable technical product mixtures are described in detail further down.

It will be appreciated that the person skilled in the art, in order to produce the different polyurethane systems, especially the different polyurethane foam types, for example hot-cure, cold-cure or ester-type flexible polyurethane foams or rigid polyurethane foams, will accordingly select the substances needed for each of these purposes, such as isocyanates, polyols, stabilizers, surfactants, etc., in order to obtain the polyurethane type, especially polyurethane foam type, desired in each case.

In the inventive production of polyurethane systems, especially of polyurethane foams, preferably at least one inventive compound of the formula (I), (II), (III), (IV), (V), (VI), (VII) and/or (VIII) and/or a corresponding quaternized and/or protonated compound, at least one polyol component and at least one isocyanate component are reacted with one another, optionally in the presence of water, physical blowing agents, flame retardants, additional catalysts and/or further additives.

Further details of the starting materials, catalysts and auxiliaries and additives used can be found, for example, in Kunststoffhandbuch [Plastics Handbook], volume 7, Polyurethane [Polyurethanes], Carl-Hanser-Verlag Munich, 1st edition 1966, 2nd edition 1983 and 3rd edition 1993. The compounds, components and additives which follow are mentioned merely by way of example and can be replaced and/or supplemented by other substances known to those skilled in the art.

The compounds of the formula (I), (II), (III), (IV), (V), (VI), (VII) and/or (VIII) and/or a correspondingly quaternized and/or protonated compound for use in accordance with the invention, in total, are used here preferably in a proportion by mass of 0.01 to 20 parts (pphp), preferably 0.01 to 5.00 parts and more preferably 0.02 to 3.00 parts, based on 100 parts (pphp) of polyol component.

Therefore, in a preferred embodiment of the invention, in the production of the polyurethane system, especially polyurethane foam, a composition including at least one nitrogen compound of the formula (I), (II), (III), (IV), (V), (VI), (VII) and/or (VIII) and/or a corresponding quaternized and/or protonated compound, and additionally at least one polyol component, at least one isocyanate component and optionally one or more blowing agents is produced, and this composition is reacted. More particularly, said nitrogen compound can also be used as a technical product mixture. Suitable technical product mixtures are described in detail further down.

The isocyanate components used are preferably one or more organic polyisocyanates having two or more isocyanate functions. Polyol components used are preferably one or more polyols having two or more isocyanate-reactive groups.

Isocyanates suitable as isocyanate components for the purposes of this invention are all isocyanates containing at least two isocyanate groups. Generally, it is possible to use all aliphatic, cycloaliphatic, arylaliphatic and preferably aromatic polyfunctional isocyanates known per se. Preferably, isocyanates are used within a range from 60 to 350 mol %, more preferably within a range from 60 to 140 mol %, relative to the sum total of the isocyanate-consuming components.

Examples include alkylene diisocyanates having 4 to 12 carbon atoms in the alkylene radical, such as dodecane 1,12-isocyanate, 2-ethyltetramethylene 1,4-diisocyanate, 2-methylpentamethylene 1,5-diisocyanate, tetramethylene 1,4-diisocyanate, and preferably hexamethylene 1,6-diisocyanate (HMDI), cycloaliphatic diisocyanates such as cyclohexane 1,3- and 1,4-diisocyanate, and any desired mixtures of these isomers, 1-isocyanato-3,3,5-trimethyl-5-isocyanatomethylcyclohexane (isophorone diisocyanate or IPDI for short), hexahydrotolylene 2,4- and 2,6-diisocyanate and the corresponding isomer mixtures, and preferably aromatic di- and polyisocyanates, for example toluene 2,4- and 2,6-diisocyanate (TDI) and the corresponding isomer mixtures, mixtures of 2,4'- and 2,2'-diphenylmethane diisocyanates (MDI) and polyphenylpolymethylene polyisocyanates (crude MDI) and mixtures of crude MDI and toluene diisocyanates (TDI). The organic di- and polyisocyanates may be used individually or in the form of mixtures thereof.

It is also possible to use isocyanates which have been modified by the incorporation of urethane, uretdione, isocyanurate, allophanate and other groups, called modified isocyanates.

Particularly suitable organic polyisocyanates, which are therefore employed with particular preference, are various isomers of toluene diisocyanate (toluene 2,4- and 2,6-diisocyanate (TDI), in pure form or as isomer mixtures of different composition), diphenylmethane 4,4'-diisocyanate (MDI), called "crude MDI" or "polymeric MDI" (containing not only the 4,4' but also the 2,4' and 2,2' isomers of MDI and higher polycyclic products), and also the bicyclic product which is referred to as "pure MDI" and is composed of predominantly 2,4' and 4,4' isomer mixtures or prepolymers thereof. Examples of particularly suitable isocyanates are detailed, for example, in EP 1712578, EP 1161474, WO 00/58383, US 2007/0072951, EP 1678232 and WO 2005/085310, to which reference is made here in full.

Polyols suitable as polyol component for the purposes of the present invention are all organic substances having two or more isocyanate-reactive groups, preferably OH groups, and also formulations thereof. Preferred polyols are any of the following which are used customarily for production of polyurethane systems, especially polyurethane foams: polyether polyols and/or polyester polyols and/or aliphatic polycarbonates containing hydroxyl groups, especially polyether carbonate polyols and/or filled polyols (polymer polyols) such as SAN, PND and PIPA polyols, these being notable in that they contain dispersed solid organic fillers up to a solids content of 40% or more, and/or autocatalytic polyols containing catalytically active functional groups, especially amino groups, and/or polyols of natural origin, called "natural oil-based polyols" (NOPs). Typically, the polyols have a functionality of 1.8 to 8 and number-average molecular weights in the range from 500 to 15 000. Typically, the polyols having OH numbers in the range from 10 to 1200 mg KOH/g are used. The number-average molecular weights are typically determined by gel permeation chromatography (GPC), especially with polypropylene glycol as reference substance and tetrahydrofuran (THF) as eluent. The OH numbers can especially be determined to DIN standard DIN 53240:1971-12.

Polyether polyols can be prepared by known processes, for example by anionic polymerization of alkylene oxides in the presence of alkali metal hydroxides, alkali metal alkoxides or amines as catalysts, and with addition of at least one starter molecule preferably containing 2 or 3 reactive hydrogens in bound form, or by cationic polymerization of alkylene oxides in the presence of Lewis acids, for example antimony pentachloride or boron trifluoride etherate, or by double metal cyanide catalysis. Suitable alkylene oxides contain 2 to 4 carbon atoms in the alkylene radical. Examples are tetrahydrofuran, 1,3-propylene oxide, 1,2- or 2,3-butylene oxide;

preference is given to using ethylene oxide and 1,2-propylene oxide. The alkylene oxides can be used individually, cumulatively, in blocks, in alternation or as mixtures. Starter molecules used may especially be compounds having at least 2, preferably 2 to 8, hydroxyl groups, or having at least two primary amino groups in the molecule. Starter molecules used may, for example, be water, di-, tri- or tetrahydric alcohols such as ethylene glycol, propane-1,2- and-1,3-diol, diethylene glycol, dipropylene glycol, glycerol, trimethylolpropane, pentaerythritol, castor oil, etc., higher polyfunctional polyols, especially sugar compounds, for example glucose, sorbitol, mannitol and sucrose, polyhydric phenols, resols, for example oligomeric condensation products of phenol and formaldehyde and Mannich condensates of phenols, formaldehyde and dialkanolamines, and also melamine, or amines such as aniline, EDA, TDA, MDA and PMDA, more preferably TDA and PMDA. The choice of the suitable starter molecule depends on the particular field of use of the resulting polyether polyol in the polyurethane production (for example, polyols used for production of flexible polyurethane foams are different from those used in the production of rigid polyurethane foams).

Polyester polyols are based on esters of polybasic aliphatic or aromatic carboxylic acids, preferably having 2 to 12 carbon atoms. Examples of aliphatic carboxylic acids are succinic acid, glutaric acid, adipic acid, suberic acid, azelaic acid, sebacic acid, decanedicarboxylic acid, maleic acid and fumaric acid. Examples of aromatic carboxylic acids are phthalic acid, isophthalic acid, terephthalic acid and the isomeric naphthalenedicarboxylic acids. The polyester polyols are obtained by condensation of these polybasic carboxylic acids with polyhydric alcohols, preferably of diols or triols having 2 to 12, more preferably having 2 to 6, carbon atoms, preferably trimethylolpropane and glycerol.

Polyether polycarbonate polyols are polyols containing carbon dioxide bound in the form of carbonate. Since carbon dioxide forms as a by-product in large volumes in many processes in the chemical industry, the use of carbon dioxide as comonomer in alkylene oxide polymerizations is of particular interest from a commercial point of view. Partial replacement of alkylene oxides in polyols with carbon dioxide has the potential to distinctly lower the costs for the production of polyols. Moreover, the use of $CO_2$ as comonomer is very advantageous in environmental terms, since this reaction constitutes the conversion of a greenhouse gas to a polymer. The preparation of polyether polycarbonate polyols by addition of alkylene oxides and carbon dioxide onto H-functional starter substances using catalysts has long been known. Various catalyst systems can be used here: The first generation was that of heterogeneous zinc or aluminum salts, as described, for example, in U.S. Pat. Nos. 3,900,424 or 3,953,383. In addition, mono- and binuclear metal complexes have been used successfully for copolymerization of CO2 and alkylene oxides (WO 2010/028362, WO 2009/130470, WO 2013/022932 or WO 2011/163133). The most important class of catalyst systems for the copolymerization of carbon dioxide and alkylene oxides is that of double metal cyanide catalysts, also referred to as DMC catalysts (U.S. Pat. No. 4,500,704, WO 2008/058913). Suitable alkylene oxides and H-functional starter substances are those which are also used for preparation of carbonate-free polyether polyols—as described above.

Polyols based on renewable raw materials, natural oil-based polyols (NOPs), for production of polyurethane foams are of increasing interest with regard to the long-term limits in the availability of fossil resources, namely oil, coal and gas, and against the background of rising crude oil prices, and have already been described many times in such applications (WO 2005/033167; US 2006/0293400, WO 2006/094227, WO 2004/096882, US 2002/0103091, WO 2006/116456 and EP 1 678 232). A number of these polyols are now available on the market from various manufacturers (WO2004/020497, US2006/0229375, WO2009/058367). Depending on the base raw material (e.g. soya bean oil, palm oil or castor oil) and the subsequent workup, polyols having a different profile of properties are the result. It is possible here to distinguish essentially between two groups: a) polyols based on renewable raw materials which are modified such that they can be used to an extent of 100% for production of polyurethanes (WO2004/020497, US2006/0229375); b) polyols based on renewable raw materials which, because of the processing and properties thereof, can replace the petrochemical-based polyol only in a certain proportion (WO2009/058367).

A further class of usable polyols is that of the so-called filled polyols (polymer polyols). A feature of these is that they contain dispersed solid organic fillers up to a solids content of 40% or more. Usable polyols include SAN, PUD and PIPA polyols. SAN polyols are highly reactive polyols containing a dispersed copolymer based on styrene-acrylonitrile (SAN). PUD polyols are highly reactive polyols containing polyurea, likewise in dispersed form. PIPA polyols are highly reactive polyols containing a dispersed polyurethane, for example formed by in situ reaction of an isocyanate with an alkanolamine in a conventional polyol.

The solids content, which is preferably between 5% and 40%, based on the polyol, depending on the application, is responsible for improved cell opening, and so the polyol can be foamed in a controlled fashion, especially with TDI, and no shrinkage of the foams occurs. The solid thus acts as an essential processing aid. A further function is to control the hardness via the solids content, since higher solids contents bring about a greater hardness on the part of the foam. The formulations with solids-containing polyols are distinctly less self-stable and therefore tend to require physical stabilization in addition to the chemical stabilization due to the crosslinking reaction. Depending on the solids contents of the polyols, these can be used for example alone or for example in a blend with the abovementioned unfilled polyols.

A further class of usable polyols is that of those which are obtained as prepolymers by reaction of polyol with isocyanate in a molar ratio of 100:1 to 5:1, preferably 50:1 to 10:1. Such prepolymers are preferably made up in the form of a solution in polymer, and the polyol preferably corresponds to the polyol used for preparing the prepolymers.

A further class of usable polyols is that of the so-called autocatalytic polyols, especially autocatalytic polyether polyols. Polyols of this kind are based, for example, on polyether blocks, preferably on ethylene oxide and/or propylene oxide blocks, and additionally include catalytically active functional groups, for example nitrogen-containing functional groups, especially amino groups, preferably tertiary amine functions, urea groups and/or heterocycles containing nitrogen atoms. Through the use of such autocatalytic polyols in the production of polyurethane systems, especially of polyurethane foams, preferably of flexible polyurethane foams, it is possible, as the case may be, to reduce the required amount of any catalysts used in addition, depending on application, and/or to match it to specific desired foam properties. Suitable polyols are described, for example, in WO0158976 (A1), WO2005063841 (A1), WO0222702 (A1), WO2006055396 (A1), WO03029320 (A1), WO0158976 (A1), U.S. Pat. No. 6,924,321 (B2), U.S. Pat. No. 6,762,274 (B2), EP2104696 (B1), WO2004060956 (A1) or WO2013102053 (A1) and can be purchased, for example, under the Voractiv™ and/or SpecFlex™ Activ trade names from Dow.

Depending on the required properties of the resulting foams, it is possible to use appropriate polyols, as described for example in: US 2007/0072951 A1, WO 2007/111828, US 2007/0238800, U.S. Pat. No. 6,359,022 or WO 96/12759. Further polyols are known to those skilled in the art and can be found, for example, in EP-A-0380993 or U.S. Pat. No. 3,346,557, to which reference is made in full.

In a preferred embodiment of the invention, especially for production of molded and highly elastic flexible foams, di- and/or trifunctional polyether alcohols are used, having primary hydroxyl groups, preferably more than 50%, more preferably more than 80%, especially those having an ethylene oxide block at the chain end. According to the required properties of this embodiment which is preferred in accordance with the invention, especially for production of the abovementioned foams, preference is given to using, as well as the polyether alcohols described here, further polyether alcohols which bear primary hydroxyl groups and are based predominantly on ethylene oxide, especially having a proportion of ethylene oxide blocks of >70%, preferably >90%. All the polyether alcohols described in the context of this preferred embodiment preferably have a functionality of 2 to 8, more preferably 2 to 5, number-average molecular weights in the range from 2500 to 15 000, preferably 4500 to 12 000, and typically OH numbers in the range from 5 to 80 and preferably 20 to 50 mg KOH/g.

In a further preferred embodiment of the invention, especially for production of slabstock flexible foams, di- and/or trifunctional polyether alcohols are used, having secondary hydroxyl groups, preferably more than 50%, more preferably more than 90%, especially those having a propylene oxide block or random propylene oxide and ethylene oxide block at the chain end, or those based only on propylene oxide blocks. Such polyether alcohols preferably have a functionality of 2 to 8, more preferably 2 to 4, number-average molecular weights in the range from 500 to 8000, preferably 800 to 5000 and more preferably 2500 to 4500, and typically OH numbers in the range from 10 to 100 and preferably 20 to 60 mg KOH/g.

In a further preferred embodiment of the invention, especially for production of polyurethane foams, preferably of flexible polyurethane foams, preferably for production of molded and highly elastic flexible foams, autocatalytic polyols as described above are used.

In a further preferred embodiment of the invention, especially for production of flexible polyurethane-polyester foams, polyester alcohols based on diols and/or triols, preferably glycerol and/or trimethylolpropane, and aliphatic carboxylic acids, preferably adipic acid, suberic acid, azelaic acid and/or sebacic acid, are used. Such polyester alcohols preferably have a functionality of 2 to 4, more preferably 2 to 3, number-average molecular weights in the range from 200-4000, preferably 400-3000 and more preferably 600-2500, and typically OH numbers in the range of 10-1000, preferably 20-500 and more preferably 30-300 mg KOH/g.

In a further preferred embodiment of the invention, especially for production of rigid polyisocyanurate (PIR) foams, polyester alcohols based on diols and/or triols, preferably monoethylene glycol, and aromatic carboxylic acids, preferably phthalic acid and/or terephthalic acid, are used. Such polyester alcohols preferably have a functionality of 2 to 4, more preferably 2 to 3, number-average molecular weights in the range from 200-1500, preferably 300-1200 and more preferably 400-1000, and typically OH numbers in the range of 100-500, preferably 150-300 and more preferably 180-250 mg KOH/g.

In a further preferred embodiment of the invention, especially for production of rigid polyurethane foams, di- to octafunctional polyether alcohols are used, having secondary hydroxyl groups, preferably more than 50%, more preferably more than 90%, especially those having a propylene oxide block or random propylene oxide and ethylene oxide block at the chain end, or those based only on propylene oxide blocks. Such polyether alcohols preferably have a functionality of 2 to 8, more preferably 3 to 8, number-average molecular weights in the range from 500 to 2000, preferably 800 to 1200, and typically OH numbers in the range from 100 to 1200, preferably 120 to 700 and more preferably 200 to 600 mg KOH/g. According to the required properties of these foams which are preferred in accordance with the invention, as well as the polyols described here, additionally polyether alcohols as described above, having greater number-average molar masses and lower OH numbers, and/or additional polyester polyols as described above, based on aromatic carboxylic acids, are used.

In a further preferred embodiment of the invention, especially for production of viscoelastic polyurethane foams, preference is given to using mixtures of various, preferably two or three, polyfunctional polyester alcohols and/or polyether alcohols. Typically, the polyol combinations used here consist of a low molecular weight "crosslinker" polyol, for example a rigid foam polyol, having high functionality (>3) and/or a conventional high molecular weight slabstock foam polyol or HR polyol and/or a "hypersoft" polyether polyol having a high proportion of ethylene oxide blocks and having cell-opening properties.

A preferred ratio of isocyanate and polyol, expressed as the index of the formulation, i.e. as stoichiometric ratio of isocyanate groups to isocyanate-reactive groups (e.g. OH groups, NH groups) multiplied by 100, is in the range from 10 to 1000, preferably 40 to 350, more preferably 70 to 140. An index of 100 represents a molar ratio of 1:1 for the reactive groups.

According to the application, it may be preferable in accordance with the invention that, in addition to the inventive nitrogen compounds of the formula (I), (II), (III), (IV), (V), (VI), (VII) and/or (VIII), and/or corresponding protonated and/or quaternized compounds, additional catalysts are used, specifically individually during the foaming or as a catalyst combination premixed with the inventive nitrogen compounds of the formula (I), (II), (III), (IV), (V), (VI), (VII) and/or (VIII), and/or corresponding protonated and/or quaternized compounds.

The expression "additional catalysts" in the context of this invention especially encompasses the use of compounds which are different from the inventive nitrogen compounds of the formula (I), (II), (III), (IV), (V), (VI), (VII) and/or (VIII) and/or corresponding protonated and/or quaternized compounds, and are simultaneously capable of catalyzing isocyanate reactions, especially the reactions mentioned hereinafter, and/or are used as catalysts, co-catalysts or activators in the production of polyisocyanate reaction products, especially in the production of polyurethane systems, more preferably in the production of polyurethane foams.

The expression "premixed catalyst combination", also referred to hereinafter as catalyst combination, in the context of this invention especially encompasses finished mixtures of inventive nitrogen compounds of the formula (I), (II), (III), (IV), (V), (VI), (VII) and/or (VIII), or corresponding protonated and/or quaternized compounds, additional catalysts, and optionally further constituents or additives, for example water, organic solvents, acids for blocking the amines, emulsifiers, surfactants, blowing agents, antioxidants, flame retardants, stabilizers and/or siloxanes, preferably polyether siloxanes, which are already present as such prior to the foaming and need not be added as individual components during the foaming operation.

Additional catalysts used in the context of this invention may, for example, be any catalysts for the isocyanate-polyol (urethane formation) and/or isocyanate-water (amine and carbon dioxide formation) and/or isocyanate dimerization (uretdione formation), isocyanate trimerization (isocyanurate formation), isocyanate-isocyanate with $CO_2$ elimination (carbodiimide formation) and/or isocyanate-amine (urea formation) reactions and/or "secondary" crosslinking reactions such as isocyanate-urethane (allophanate formation) and/or isocyanate-urea (biuret formation) and/or isocyanate-carbodiimide (uretonimine formation).

Suitable additional catalysts for the purposes of the present invention are, for example, substances which catalyze one of the aforementioned reactions, especially the gel reaction (isocyanate-polyol), the blowing reaction (isocyanate-water) and/or the dimerization or trimerization of the isocyanate. Such catalysts are preferably nitrogen compounds, especially amines and ammonium salts, and/or metal compounds.

Suitable nitrogen compounds as additional catalysts for the purposes of the present invention are all nitrogen compounds according to the prior art which are different from the inventive nitrogen compounds of the formulae (I) to (VIII), which catalyze one of the abovementioned isocyanate reactions and/or can be used for production of polyurethanes, especially of polyurethane foams.

The expression "nitrogen compounds of the formula (I)" in the context of this invention encompasses the corresponding protonated and/or quaternized compounds in each case, and also mixtures of these compounds. The expression "nitrogen compounds of the formula (I), (II), (III), (IV), (V), (VI), (VII) and/or (VIII)" in the context of this invention encompasses the corresponding protonated and/or quaternized compounds in each case, and also mixtures of these compounds. The expression "at least one nitrogen compound of the formula (I), (II), (III), (IV), (V), (VI), (VII) and/or (VIII)" in the context of this invention also encompasses the combined use of such nitrogen compounds, i.e., for example, the combined use of nitrogen compounds of the formulae (III) and (IV).

Examples of suitable additional nitrogen compounds as catalysts for the purposes of the present invention are the amines triethylamine, N,N-dimethylcyclohexylamine, N,N-dicyclohexylmethylamine, N,N-dimethylaminoethylamine, N,N,N',N'-tetramethylethylene-1,2-diamine, N,N,N',N'-tetramethylpropylene-1,3-diamine, N,N,N',N'-tetramethyl-1,4-butanediamine, N,N,N',N'-tetramethyl-1,6-hexanediamine, N,N,N',N'',N''-pentamethyldiethylenetriamine, N,N,N'-trimethylaminoethylethanolamine, N,N-dimethylaminopropylamine, N,N-diethylaminopropylamine, 1-(2-aminoethyl)pyrrolidine, 1-(3-aminopropyl)pyrrolidine, N,N-dimethylaminopropyl-N',N'-dipropan-2-olamine, 2-[[3-(dimethylamino)propyl]methylamino]ethanol, 3-(2-dimethylamino)ethoxy)propylamine, N,N-bis[3-(dimethylamino)propyl]amine, N,N,N',N'',N''-pentamethyldipropylenetriamine, 1-[bis[3-(dimethylamino)propyl]amino]-2-propanol, N,N-bis[3-(dimethylamino)propyl]-N',N'-dimethylpropane-1,3-diamine, triethylenediamine, 1,4-diazabicyclo[2.2.2]octane-2-methanol, N,N'-dimethylpiperazine, 1,2-dimethylimidazole, N-(2-hydroxypropyl)imidazole, 1-isobutyl-2-methylimidazole, N-(3-aminopropyl)imidazole, N-methylimidazole, N-ethylmorpholine, N-methylmorpholine, 2,2,4-trimethyl-2-silamorpholine, N-ethyl-2,2-dimethyl-2-silamorpholine, N-(2-aminoethyl)morpholine, N-(2-hydroxyethyl)morpholine, 2,2'-dimorpholinodiethyl ether, N,N'-dimethylpiperazine, N-(2-hydroxyethyl)piperazine, N-(2-aminoethyl)piperazine, N,N-dimethylbenzylamine, N,N-dimethylaminoethanol, N,N-diethylaminoethanol, 1-(2-hydroxyethyl)pyrrolidine, 3-dimethylamino-1-propanol, 1-(3-hydroxypropyl)pyrrolidine, N,N-dimethylaminoethoxyethanol, N,N-diethylaminoethoxyethanol, bis(2-dimethylaminoethyl) ether), N,N,N'-trimethyl-N'-(2-hydroxyethyl)bis(2-aminoethyl) ether, N,N,N'-trimethyl-N-3'-aminopropyl(bisaminoethyl)ether, tris(dimethylaminopropyl)hexahydro-1,3,5-triazine, 1,8-diazabicyclo[5.4.0]undec-7-ene, 1,5-diazabicyclo[4.3.0]non-5-ene, 1,5,7-triazabicyclo[4.4.0]dec-5-ene, N-methyl-1,5,7-triazabicyclo[4.4.0]dec-5-ene, 1,4,6-triazabicyclo[3.3.0]oct-4-ene, 1,1,3,3-tetramethylguanidine, tert-butyl-1,1,3,3-tetramethylguanidine, guanidine, 3-dimethylaminopropylurea, 1,3-bis[3-(dimethylamino)propyl]urea, bis-N,N-(dimethylaminoethoxyethyl)isophoronedicarbamate, 3-dimethylamino-N,N-dimethylpropionamide and 2,4,6-tris(dimethylaminomethyl)phenol. Suitable additional nitrogen-containing catalysts according to the prior art can be purchased, for example, from Evonik under the TEGOAMIN® trade name.

Suitable metal compounds as additional catalysts for the purposes of the present invention are all metal compounds according to the prior art which catalyze one of the abovementioned isocyanate reactions and/or can be used for production of polyurethanes, especially of polyurethane foams, alongside the inventive nitrogen compounds of the formulae (I) to (VIII). They may be selected, for example, from the group of the metal-organic or organometallic compounds, metal-organic or organometallic salts, organic metal salts, inorganic metal salts, and from the group of the charged or uncharged metallic coordination compounds, especially the metal chelate complexes.

The expression "metal-organic or organometallic compounds" in the context of this invention especially encompasses the use of metal compounds having a direct carbon-metal bond, also referred to here as metal organyls (e.g. tin organyls) or organometallic compounds (e.g. organotin compounds). The expression "organometallic or metal-organic salts" in the context of this invention especially encompasses the use of metal-organic or organometallic compounds having salt character, i.e. ionic compounds in which either the anion or cation is organometallic in nature (e.g. organotin oxides, organotin chlorides or organotin carboxylates). The expression "organic metal salts" in the context of this invention especially encompasses the use of metal compounds which do not have any direct carbon-metal bond and are simultaneously metal salts, in which either the anion or the cation is an organic compound (e.g. tin(II) carboxylates). The expression "inorganic metal salts" in the context of this invention especially encompasses the use of metal compounds or of metal salts in which neither the anion nor the cation is an organic compound, e.g. metal chlorides (e.g. tin(II) chloride), pure metal oxides (e.g. tin oxides) or mixed metal oxides, i.e. containing a plurality of metals, and/or metal silicates or aluminosilicates. The expression "coordination compound" in the context of this invention especially encompasses the use of metal compounds formed from one or more central particles and one or more ligands, the central particles being charged or uncharged metals (e.g. metal- or tin-amine complexes). The expression "metal-chelate complexes" in the context of this invention especially encompasses the use of metallic coordination compounds having ligands having at least two coordination or bonding sites to the metal center (e.g. metal- or tin-polyamine or metal- or tin-polyether complexes).

Suitable metal compounds, especially as defined above, as additional catalysts for the purposes of the present invention may, for example, be selected from all metal compounds containing lithium, sodium, potassium, magnesium, calcium, scandium, yttrium, titanium, zirconium, vanadium, niobium, chromium, molybdenum, tungsten, manganese, cobalt, nickel, copper, zinc, mercury, aluminum, gallium, indium, germanium, tin, lead and/or bismuth, especially sodium, potassium, magnesium, calcium, titanium, zirconium, molybdenum, tungsten, zinc, aluminum, tin and/or bismuth, more preferably tin, bismuth, zinc and/or calcium.

Suitable inorganic metal salts, especially as defined above, as additional catalysts for the purposes of the present invention may be selected, for example, from the group of the salts of inorganic acids, for example hydrochloric acid, carbonic acid, sulphuric acid, nitric acid and phosphoric acid, and/or of further halogen-containing acids. The resulting inorganic metal salts, for example metal chlorides, metal sulphates, metal phosphates, preferably metal chlorides such as tin(II) chloride, can be used in the production of polyurethane systems, especially of polyurethane foams, generally only in combination with other organometallic salts, organic metal salts or nitrogen-containing catalysts, and not as sole catalysts, in pure form or blended in a solvent.

Suitable charged or uncharged metallic coordination compounds, especially the metal chelate complexes, especially as defined above, as additional catalysts for the purposes of the present invention may, for example, be selected from the group of the mono- or polynuclear metal-amine, metal-polyamine, metal-polyether, metal-polyester and/or metal-polyamine-polyether complexes. Such complexes can be formed either in situ during the foaming and/or prior to the foaming, or be used as isolated complexes, in pure form or blended in a solvent. Suitable complexing agents, ligands and/or chelate ligands include, for example, acetylacetone, benzoyl acetone, trifluoroacetyl acetone, ethyl acetoacetate, salicylaldehyde, salicylaldehyde imine and other Schiff bases, cyclopentanone-2-carboxylate, pyrrolidones, for example N-methyl-2-pyrrolidone, N-ethyl-2-pyrrolidone and polyvinylpyrrolidones (various molar mass distributions), polyethers of various molar masses, cyclic polyethers, for example crown ethers, and diamines and polyamines containing primary, secondary and/or tertiary amines.

Suitable metallic coordination compounds are, for example, all metal acetylacetonates such as nickel(II) acetylacetonate, zinc (II) acetylacetonate, copper(II) acetylacetonate, molybdenum dioxoacetylacetonate, all iron acetylacetonates, all cobalt acetylacetonates, all zirconium acetylacetonates, all titanium acetylacetonates, all bismuth acetylacetonates and all tin acetylacetonates.

Suitable organometallic salts and organic metal salts, especially as defined above, as additional catalysts for the purposes of the present invention may be selected, for example, from the group of the salts of organic acids.

The expression "organic acids" in the context of this invention encompasses all organochemical, i.e. carbon-containing, compounds having a functional group which can enter into an equilibrium reaction with water and other protonatable solvents in the manner of an acid-base reaction.

Suitable organic acids may be selected, for example, from the group of carboxylic acids, i.e. organic compounds bearing one or more carboxyl groups (*—COOH), called carboxylates, and/or of alcohols, i.e. organic compounds bearing one or more hydroxyl groups (*—OH), called alkoxides, and/or of thiols, i.e. organic compounds bearing one or more thiol groups (*—SH, also referred to as mercapto groups in molecules having higher-priority functional groups), called thiolates (or mercaptides), and/or of mercaptoacetic esters as a special case of the thiols, i.e. organic compounds bearing one or more mercaptoacetic ester groups (*—O—CO—CH$_2$—CH$_2$—SH), called mercaptoacetates, and/or of sulphuric esters, i.e. organic compounds bearing one or more sulphate groups (*—O—SO$_3$H), called sulphates, and/or of sulphonic acids, i.e. organic compounds bearing one or more sulpho groups (*—SO$_2$—OH), called sulphonates, and/or phosphoric esters (alkyl phosphates), i.e. organic compounds which are alkyl mono- or diesters of orthophosphoric acid (*—O—PO(OH)$_2$ or *—O—PO(OR)OH), called phosphates, and/or of phosphonic acids, i.e. organic compounds bearing one or more phosphonic acid groups (*—PO(OH)$_2$), called phosphonates, and/or phosphorous esters, organic compounds which are alkyl esters of phosphonic acid (*—P(OR)$_2$(OH) or *—P(OR)(OH)$_2$), called phosphites.

Suitable carboxylic acids for the purposes of the present invention are, for example, all linear, branched or cyclic, aliphatic or aromatic, saturated or unsaturated mono-, di- or polycarboxylic acids which are optionally substituted by one or more heteroatoms, preferably by hydroxyl groups (*—OH), primary, secondary or tertiary amino groups (*—NH$_2$, *—NHR, *—NR$_2$) or mercapto groups (*—SH), or interrupted by one or more heteroatoms. Particularly suitable in the context of the present invention are carboxylic acids having, bonded to the carbonyl carbon atom thereof, a hydrogen atom or a linear, branched or cyclic, aliphatic, saturated or unsaturated hydrocarbyl radical which is optionally substituted by one or more heteroatoms, preferably by hydroxyl groups (*—OH), primary, secondary or tertiary amino groups (*—NH$_2$, *—NHR, *—NR$_2$) or mercapto groups (*—SH), or interrupted by one or more heteroatoms. Particularly suitable in the context of the present invention are those aliphatic carboxylic acids having, in the 2 position, i.e. on the carbon atom next to the carbonyl function, disubstituted (tertiary) or trisubstituted (quaternary) carbons, or corresponding hydrocarbyl radicals. Preference is given in the context of the present invention to those aliphatic carboxylic acids having, in the 2 position, one or two methyl, ethyl, n-propyl, isopropyl, n-butyl and/or isobutyl branch(es). Particular preference is given in the context of the present invention to those aliphatic carboxylic acids, especially monocarboxylic acids, which, as well as the described branch in the 2 position, have a saturated or unsaturated, linear or branched alkyl chain and optionally substituted by one or more heteroatoms, preferably by hydroxyl groups (*—OH), primary, secondary or tertiary amino groups (*—NH$_2$, *—NHR, *—NR) or mercapto groups (*—SH). More particularly, suitable carboxylic acids may be selected from the group of the neo acids or Koch acids.

Examples of suitable mono-, di- and polybasic, saturated and unsaturated, substituted and unsubstituted carboxylic acids, fatty acids and neo acids or Koch acids are carboxylic acids such as formic acid, acetic acid, propionic acid, acrylic acid, butyric acid, isobutyric acid, 2,2-dimethylbutyric acid, valeric acid, isovaleric acid, 2-methylvaleric acid, 2,2-dimethylvaleric acid (isoheptanoic acid), pivalic acid, caproic acid, 2-ethylhexanoic acid (isooctanoic acid), oenanthic acid, caprylic acid, pelargonic acid, isononanoic acid, 3,5,5-trimethylhexanoic acid, 2,5,5-trimethylhexanoic acid, 4,5,5-trimethylhexanoic acid, 2,2,4,4-tetramethylpentanoic acid, 6,6-dimethylheptanoic acid, capric acid, neodecanoic acid, 7,7-dimethyloctanoic acid, 2,2-dimethyloctanoic acid, 2,4-dimethyl-2-i sopropylpentanoic acid, 2,2,3,5-tetramethylhexanoic acid, 2,2-diethylhexanoic acid, 2,5-dimethyl-2-ethylhexanoic acid, undecanoic acid, lauric acid, tridecanoic acid, neotridecanoic acid, myristic acid, pentadecanoic acid, palmitic acid, margaric acid, stearic acid, oleic acid, linoleic acid, alpha-linolenic acid, phytanic acid, eicosenoic acid, erucic acid, ricinoleic acid, vernolic acid, arachic acid, arachidonic acid, oxalic acid, glycolic acid, glyoxalic acid, malonic acid, lactic acid, citric acid, succinic acid, fumaric acid, maleic acid, malic acid, tartaric acid, glutaric acid, adipic acid, sorbic acid, cinnamic acid, salicylic acid, benzoic acid, terephthalic acid, phthalic acid, isophthalic acid, nicotinic acid, carbamic acid, pyrrolidine-2-carboxylic acid and cyclohexanecarboxylic acid.

Suitable alcohols are all linear, branched or cyclic, aliphatic or aromatic, saturated or unsaturated monohydric alcohols, dihydric alcohols (diols) and/or polyhydric alcohols (polyols) which are optionally substituted by one or more heteroatoms, preferably by primary, secondary or tertiary amino groups (*—$NH_2$, *—NHR, *—$NR_2$) or mercapto groups (*—SH), or interrupted by one or more heteroatoms. Suitable examples for this purpose are methanol, ethanol, propanol, isopropanol, butanol, tert-butanol, neopentyl alcohol, phenols and/or nonylphenol.

Suitable thiols, mercaptoacetic esters, sulphuric esters, sulphonic acids, phosphonic esters (alkyl phosphates), phosphonic acids and/or phosphorous esters are, for example, all linear, branched or cyclic, aliphatic or aromatic, saturated or unsaturated organic compounds which are optionally substituted by one or more heteroatoms or interrupted by one or more heteroatoms and contain one or more appropriate functional groups, as defined above. Suitable examples for this purpose are dialkyl phosphites, methanesulphonic acid, trifluoromethanesulphonic acid, p-toluenesulphonic acid, dodecylbenzenesulphonic acid, taurine, isooctyl mercaptoacetate, 2-ethylhexyl mercaptoacetate, ethanethiol and/or n-lauryl mercaptide.

Particularly suitable organometallic salts and organic metal salts as defined above, as additional catalysts for the purposes of the present invention, are, for example, organotin, tin, zinc, bismuth and potassium salts, especially corresponding metal carboxylates, alkoxides, thiolates and mercaptoacetates, for example dibutyltin diacetate, dimethyltin dilaurate, dibutyltin dilaurate (DBTDL), dioctyltin dilaurate (DOTDL), dimethyltin dineodecanoate, dibutyltin dineodecanoate, dioctyltin dineodecanoate, dibutyltin dioleate, dibutyltin bis-n-laurylmercaptide, dimethyltin bis-n-laurylmercaptide, monomethyltin tris-2-ethylhexylmercaptoacetate, dimethyltin bis-2-ethylhexylmercaptoacetate, dibutyltin bis-2-ethylhexylmercaptoacetate, dioctyltin bisisooctylmercaptoacetate, tin(II) acetate, tin(II) 2-ethylhexanoate (tin(II) octoate), tin(II) isononanoate (tin(II) 3,5,5-trimethylhexanoate), tin(II) neodecanoate, tin(II) ricinoleate, zinc(II) acetate, zinc(II) 2-ethylhexanoate (zinc(II) octoate), zinc(II) isononanoate (zinc(II) 3,5,5-trimethylhexanoate), zinc(II) neodecanoate, zinc(II) ricinoleate, bismuth acetate, bismuth 2-ethylhexanoate, bismuth octoate, bismuth isononanoate, bismuth neodecanoate, potassium formate, potassium acetate, potassium 2-ethylhexanoate (potassium octoate), potassium isononanoate, potassium neodecanoate and/or potassium ricinoleate.

In the inventive production of polyurethanes, according to the manner of use, especially in the production of polyurethane foams, it may be preferable to rule out the use of organometallic salts, for example dibutyltin dilaurate.

Suitable additional metallic catalysts are generally and preferably selected such that they do not have any troublesome intrinsic odor and are essentially toxicologically safe, and such that the resulting polyurethane systems, especially polyurethane foams, have a minimum level of catalyst-related emissions.

Aside from additional amines and metal compounds, it is also possible to use ammonium salts as additional catalysts. Suitable examples are ammonium formate and/or ammonium acetate.

Suitable additional catalysts are mentioned, for example, in DE 102007046860, EP 1985642, EP 1985644, EP 1977825, US 2008/0234402, EP 0656382 B1 and US 2007/0282026 A1, and the patent specifications cited therein.

Suitable use amounts of additional catalysts are guided by the type of catalyst and are preferably in the range from 0.01 to 10.0 pphp, more preferably in the range from 0.02 to 5.00 pphp (=parts by weight based on 100 parts by weight of polyol) or 0.10 to 10.0 pphp for potassium salts.

According to the application, it may be preferable in accordance with the invention when, in the case of use of additional catalysts and/or of premixed catalyst combinations, as defined above, the sum total of all the nitrogen compounds used, i.e. the sum total of the inventive nitrogen compounds of the formula (I), (II), (III), (IV), (V), (VI), (VII) and/or (VIII) and the additional nitrogen-containing catalysts according to the prior art, relative to the sum total of the metallic catalysts, especially potassium, zinc and/or tin catalysts, results in a molar ratio of 1:0.05 to 0.05:1, preferably 1:0.07 to 0.07:1 and more preferably 1:0.1 to 0.1:1.

It may be preferable in accordance with the invention that additional catalysts and/or premixed catalyst combinations, as defined above, are free of dimethylamine-bearing nitrogen compounds. Catalyst combinations are free of dimethylamine-bearing nitrogen compounds for the purposes of this invention preferably when less than 75% by weight, especially less than 50% by weight, preferably less than 30% by weight, more preferably less than 10% by weight, of the catalysts in the catalyst mixture include dimethylamine-bearing nitrogen compounds. Especially preferred are catalyst combinations which contain absolutely no, i.e. 0% by weight of, dimethylamine-bearing nitrogen compounds.

In order to prevent any reaction of the components with one another, especially reaction of nitrogen compounds of the formula (I), (II), (III), (IV), (V), (VI), (VII) and/or (VIII) used in accordance with the invention and/or additional nitrogen-containing catalysts with additional metallic catalysts, especially potassium, zinc and/or tin catalysts, it may be preferable to store these components separately from one another and then to feed in the isocyanate and polyol reaction mixture simultaneously or successively.

In a preferred embodiment of the invention, in the context of the inventive use, at least one nitrogen compound of the formula (I), (II), (III), (IV), (V), (VI), (VII) and/or (VIII) and/or a corresponding quaternized and/or protonated compound is used in combination with a) one or more additional (i.e. noninventive) nitrogen compounds as additional catalysts, preferably as defined and described by way of example above, b) one or more additional metallic catalysts, especially one or more tin, zinc, bismuth and/or potassium compounds, preferably as defined and described by way of example above, c) one or more acids to block the amines present, preferably as described above, d) water, e) one or more organic solvents, preferably as defined and described by way of example hereinafter, f) one or more chemical or physical blowing agents, preferably as described hereinafter, g) one or more stabilizers against oxidative degradation, for example antioxidants, preferably as described hereinafter, h) one or more flame retardants, preferably as described hereinafter, and/or i) one or more foam stabilizers based on siloxanes and/or polydialkylsiloxane-polyoxyalkylene copolymers, preferably as defined and described hereinafter, and/or j) one or more further additives, for example selected from the group of the surfactants, biocides, dyes, pigments, fillers, antistatic additives, crosslinkers, chain extenders, cell openers and/or fragrances, wherein the production of the polyurethane, especially the polyurethane foam, is advantageously preceded by initial production of a composition, for example in the manner of pre-dosage of the individual components in the mixing head or as a premixed catalyst combination, as defined above, comprising the aforementioned combination. More particularly, said nitrogen compound of the formula (I), (II), (III), (IV), (V), (VI), (VII) and/or (VIII) can also be used as a technical product mixture. Suitable technical product mixtures have been elucidated in the description.

For the purposes of the aforementioned preferred embodiment, particularly preferred combinations in the context of the present invention are those compositions in which at least one nitrogen compound of the formula (I), (II), (III), (IV), (V), (VI), (VII) and/or (VIII) and/or a corresponding quaternized and/or protonated compound is used in combination with a), with b), with c), with d), with e), with f), with a), b), c), d) e) and f), with a) and b), with a) and c), with a), b) and c), with a), b) and d), with a), b) and e), with a), b), d) and e), with a), b), d), e) and f), with a), b), e) and f), with a), c) and d), with a), c) and e), with a), c), d) and e), with a), b) and e), with a), b), c) and e), with a), b), c), d) and e), with c) and d), with c) and e), with c), d) and e), with c), e) and f), with c), d), e) and f), with c), d), e) and f), with b) and c), with b), c) and d), with b), c) and e), with b), c), d) and e), with b), c), e) and f), with b), c), d), e), f), with b) and d), with b) and e), with b), d) and e), with b), d) and f), with b), e) and f), or with b), d), e) and f).

The inventive compounds of the formulae (I), (II), (III), (IV), (V), (VI), (VII) and/or (VIII) or the corresponding protonated and/or quaternized compounds can be used as a pure substance or in a blend, for example with suitable solvents and/or further additives, individually during the foaming or in the form of a premixed catalyst combination, as defined above.

Useful solvents are all substances suitable according to the prior art. According to the application, it is possible to use aprotic nonpolar, aprotic polar and protic solvents. Suitable aprotic nonpolar solvents may be selected, for example, from the following substance classes, or substance classes containing the following functional groups: aromatic hydrocarbons, aliphatic hydrocarbons (alkanes (paraffins) and olefins), carboxylic esters and polyesters, (poly)ethers and/or halogenated hydrocarbons of low polarity. Suitable aprotic polar solvents may be selected, for example, from the following substance classes, or substance classes containing the following functional groups: ketones, lactones, lactams, nitriles, carboxamides, sulphoxides and/or sulphones. Suitable protic solvents may be selected, for example, from the following substance classes, or substance classes containing the following functional groups: alcohols, polyols, (poly)alkylene glycols, amines, carboxylic acids, especially fatty acids, and/or primary and secondary amides.

Preferred solvents are, for example, mineral oils, hexane, pentane, heptane, decane or mixtures of saturated hydrocarbons, for example Kaydol products from Sonneborn, glycol ethers such as ethylene glycol dimethyl ether (monoglyme), bis(2-methoxyethyl) ether (diglyme), triethylene glycol dimethyl ether (triglyme), tetraethylene glycol dimethyl ether (tetraglyme), polyester and polyether polyols, polyols based on renewable raw materials (NOPs), end-capped polyethers, preferably dialkyl polyethers having, as alkyl radicals, butyl/methyl, methyl/methyl or butyl/butyl radicals, preferably those obtainable from diol-started polyethers, glycols, glycerol, carboxylic esters, preferably fatty acid esters, for example ethyl acetate and isopropyl myristate, polycarbonates, phthalates, preferably dibutyl phthalate (DBP), dioctyl phthalate (DNOP), diethylhexyl phthalate (DEHP), diisononyl phthalate (DINP), dimethyl phthalate (DMP), diethyl phthalate (DEP), cyclohexanoates, preferably diisononyl cyclohexanoate (DINCH).

Particularly preferred solvents are compounds which can be processed without any problem in the foaming operation and do not adversely affect the properties of the foam. For example, isocyanate-reactive compounds are suitable, since they are incorporated into the polymer matrix by reaction and do not generate any emissions in the foam. Examples are OH-functional compounds such as (poly)alkylene glycols, preferably monoethylene glycol (MEG or EG), diethylene glycol (DEG), triethylene glycol (TEG), 1,2-propylene glycol (PG), dipropylene glycol (DPG), trimethylene glycol (propane-1,3-diol, PDO), tetramethylene glycol (butanediol, BDO), butyl diglycol (BDG), neopentyl glycol, 2-methylpropane-1,3-diol (Ortegol CXT) and higher homologues thereof, for example polyethylene glycol (PEG) having mean molar masses between 200 and 3000. Further particularly preferred OH-functional compounds are polyethers having mean molar masses of 200 to 4500, especially 400 to 2000, and among these preferably water-, allyl-, butyl- or nonyl-started polyethers, especially those based on propylene oxide (PO) and/or ethylene oxide (EO) blocks.

If, in a preferred embodiment, the at least one nitrogen compound of the formula (I), preferably of the formula (II), (III), (IV), (V), (VI), (VII) and/or (VIII), is used in combination with at least one solvent, the mass ratio of the total amount of catalyst used, comprising all the catalytically active compounds of the formula (I) and not of the formula (I), to solvent is preferably from 100:1 to 1:4, preferably from 50:1 to 1:3 and more preferably from 25:1 to 1:2.

Additives used may be all substances which are known according to the prior art and find use in the production of polyurethanes, especially of polyurethane foams, for example blowing agents, preferably water for formation of $CO_2$, and, if necessary, further physical blowing agents, crosslinkers and chain extenders, stabilizers against oxidative degradation (called antioxidants), flame retardants, surfactants, biocides, cell-refining additives, cell openers, solid fillers, antistatic additives, nucleating agents, thickeners, dyes, pigments, color pastes, fragrances, emulsifiers, buffer substances and/or additional catalytically active substances, especially as defined above.

If polyurethane foams are to be used as polyurethane systems, it may be advantageous to use water as blowing agent. Preference is given to using a sufficient amount of water that the amount of water is 0.10 to 25.0 pphp (pphp=parts by weight based on 100 parts by weight of polyol).

It is also possible to use suitable physical blowing agents. These are, for example, liquefied $CO_2$, and volatile liquids, for example hydrocarbons of 3, 4 or 5 carbon atoms, preferably cyclo-, iso- and n-pentane, hydrofluorocarbons, preferably HFC 245fa, HFC 134a and HFC 365mfc, hydrochlorofluorocarbons, preferably HCFC 141b, hydrofluoroolefins (HFO) or hydrohaloolefins, for example 1234ze, 1233zd(E) or 1336mzz, oxygen compounds such as methyl formate, acetone and dimethoxymethane, or hydrochlorocarbons, preferably dichloromethane and 1,2-dichloroethane.

In addition to water and the physical blowing agents, it is also possible to use other chemical blowing agents which react with isocyanates to evolve a gas, an example being formic acid.

Crosslinkers and chain extenders refer to low molecular weight polyfunctional compounds that are reactive toward isocyanates. Suitable examples are hydroxyl- or amine-terminated substances such as glycerol, neopentyl glycol, 2-methylpropane-1,3-diol, triethanolamine (TEOA), diethanolamine (DEOA) and trimethylolpropane. The use concentration is typically between 0.1 and 5 parts, based on 100 parts polyol, but may also differ therefrom according to the formulation. When crude MDI is used, it likewise assumes a crosslinking function in the foam-in-place operation. The content of low molecular weight crosslinkers can therefore be reduced correspondingly with an increasing amount of crude MDI.

Suitable stabilizers against oxidative degradation, called antioxidants, are preferably all standard free-radical scavengers, peroxide scavengers, UV absorbers, light stabilizers, complexing agents for metal ion contaminants (metal deactivators). Compounds usable with preference are from the following substance classes, or substance classes containing the following functional groups, where preferred substituents on the respective base structures are especially those having groups reactive toward isocyanate: 2-(2'-hydroxyphenyl)benzotriazoles, 2-hydroxybenzophenones, benzoic acids and benzoates, phenols, especially containing tert-butyl and/or methyl substituents on the aromatic ring, benzofuranones, diarylamines, triazines, 2,2,6,6-tetramethylpiperidines, hydroxylamines, alkyl and aryl phosphites, sulphides, zinc carboxylates, diketones. Phenols used may, for example, be esters based on 3-(4-hydroxyphenyl)propionic acid such as triethylene glycol bis[3-(3-tert-butyl-4-hydroxy-5-methylphenyl)propionate], octadecyl 3-(3,5-di-tert-butyl-4-hydroxyphenyl)propionate, or methylenediphenols such as 4,4'-butylidenebis(6-tert-butyl-3-methylphenol). Preferred 2-(2'-hydroxyphenyl)benzotriazoles are, for example, 2-(2'-hydroxy-5-methylphenyl)benzotriazole or 2-(2'-hydroxy-3',5'-di-tert-butylphenyl)benzotriazole. Preferred 2-hydroxybenzophenones are, for example, 2-hydroxy-4-n-octoxybenzophenone, 2,2',4,4'-tetrahydroxybenzophenone or 2,4-dihydroxybenzophenone. Preferred benzoates are, for example, hexadecyl 3,5-di-tert-butyl-4-hydroxybenzoate or tannins.

Suitable flame retardants in the context of this invention are all substances which are regarded as suitable for this purpose according to the prior art. Preferred flame retardants are, for example, liquid organophosphorus compounds such as halogen-free organophosphates, e.g. triethyl phosphate (TEP), halogenated phosphates, for example tris(1-chloro-2-propyl) phosphate (TCPP) and tris(2-chloroethyl) phosphate (TCEP), and organic phosphonates, for example dimethyl methanephosphonate (DMMP), dimethyl propanephosphonate (DMPP), or solids such as ammonium polyphosphate (APP) and red phosphorus. Suitable flame retardants further include halogenated compounds, for example halogenated polyols, and also solids such as expandable graphite and melamine.

Surfactants, which are used especially in the production of polyurethane foams, may be selected, for example, from the group comprising anionic surfactants, cationic surfactants, nonionic surfactants and/or amphoteric surfactants. Surfactants used may, in accordance with the invention, also be polymeric emulsifiers such as polyalkyl polyoxyalkyl polyacrylates, polyvinylpyrrolidones or polyvinyl acetates.

Biocides used may, for example, be commercial products such as chlorophene, benzisothiazoline, hexahydro-1,3,5-tris(hydroxyethyl-s-triazine), chloromethylisothiazoline, methylisothiazoline or 1,6-dihydroxy-2,5-dioxohexane, which are known by the trade names BIT 10, Nipacide BCP, Acticide MBS, Nipacide BK, Nipacide CI, Nipacide FC.

The foam properties of polyurethane foams can be influenced in the course of production thereof especially using siloxanes or organomodified siloxanes, for which it is possible to use the substances known in the prior art. Preference is given to using those compounds that are particularly suitable for the respective foam types (rigid foams, hot-cure flexible foams, viscoelastic foams, ester foams, cold-cure flexible foams (HR foams), semirigid foams). Suitable (organomodified) siloxanes are described for example in the following documents: EP 0839852, EP 1544235, DE 102004001408, EP 0839852, WO 2005/118668, US 20070072951, DE 2533074, EP 1537159 EP 533202, US 3933695, EP 0780414, DE 4239054, DE 4229402, EP 867465. These compounds may be prepared as described in the prior art. Suitable examples are described for instance in U.S. Pat. No. 4,147,847, EP 0493836 and U.S. Pat. No. 4,855,379.

(Foam) stabilizers may be all stabilizers known from the prior art. Preference is given to using foam stabilizers based on polydialkylsiloxane-polyoxyalkylene copolymers, as generally used in the production of urethane foams. The structure of these compounds is preferably such that, for example, a long-chain copolymer of ethylene oxide and propylene oxide is bonded to a polydimethylsiloxane radical. The linkage between the polydialkylsiloxane and the polyether moiety may be via an SiC linkage or an Si—O—C bond. In structural terms, the polyether or the different polyethers may be bonded to the polydialkylsiloxane in terminal or lateral positions. The alkyl radical or the various alkyl radicals may be aliphatic, cycloaliphatic or aromatic. Methyl groups are very particularly advantageous. The polydialkylsiloxane may be linear or else contain branches. Suitable stabilizers, especially foam stabilizers, are described inter alia in U.S. Pat. Nos. 2,834,748, 2,917,480 and in 3,629,308. Suitable stabilizers can be purchased from Evonik Industries AG under the TEGOSTAB® trade name.

Suitable siloxanes which can be used in the case of the inventive use of the nitrogen compounds of the formula (I), (II), (III), (IV), (V), (VI), (VII) and/or (VIII) and/or the corresponding quaternized and/or protonated compounds in the production of polyurethane foams especially have the following structure:

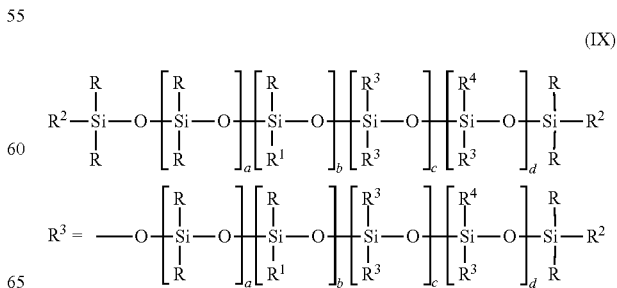

in which a is independently 0 to 500, preferably 1 to 300 and especially 2 to 150, b is independently 0 to 60, preferably 1 to 50 and especially 1 to 30, c is independently 0 to 10, preferably 0 or >0 to 5, d is independently 0 to 10, preferably 0 or >0 to 5, with the proviso that, for each molecule of the formula (IX), the mean number $\Sigma d$ of T units [SiR$^3$R$^4$O] and the mean number $\Sigma c$ of Q units [SiR$^3$R$^3$O] per molecule is not greater than 50 in either case, the mean number $\Sigma a$ of D units [SiRRO] per molecule is not greater than 2000 and the mean number $\Sigma b$ of the siloxy units bearing R$^1$ per molecule is not greater than 100, R is independently at least one radical from the group of linear, cyclic or branched, aliphatic or aromatic, saturated or unsaturated hydrocarbyl radicals having 1 up to 20 carbon atoms, but is preferably a methyl radical, R$^2$ is independently R$^1$ or R, R$^1$ is different from R and is independently an organic radical and/or a polyether radical, R$^1$ preferably being a radical selected from the group of —CH$_2$—CH$_2$—CH$_2$—O—(CH$_2$—CH$_2$O—)$_x$—(CH$_2$—CH(R')O—)$_y$—R"

—CH$_2$—CH$_2$—O—(CH$_2$—CH$_2$O—)$_x$—(CH$_2$—CH(R')O—)$_y$—R"

—O—(C$_2$H$_4$O—)$_x$—(C$_3$H$_5$O—)$_y$—R'

—CH$_2$—R$^{IV}$

—CH$_2$—CH$_2$—(O)$_{x'}$—R$^{IV}$

—CH$_2$—CH$_2$—CH$_2$—O—CH$_2$—CH(OH)—CH$_2$OH

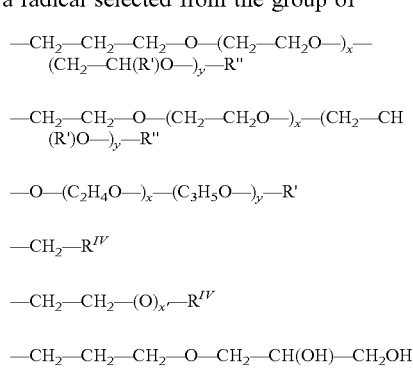

or

—CH$_2$—CH$_2$—CH$_2$—O—CH$_2$—C(CH$_2$OH)$_2$—CH$_2$—CH$_3$, in which x is 0 to 100, preferably >0, especially 1 to 50, x' is 0 or 1, y is 0 to 100, preferably >0, especially 1 to 50, z is 0 to 100, preferably >0, especially 1 to 10, R' is independently an optionally substituted alkyl or aryl group having 1 to 12 carbon atoms, substituted, for example, by alkyl radicals, aryl radicals or haloalkyl or haloaryl radicals, where different R' substituents may be present within any R$^1$ radical and/or any molecule, and R" is independently a hydrogen radical or an alkyl group having 1 to 4 carbon atoms, a —C(O)—R'" group with R'"=alkyl radical, a —CH$_2$—O—R' group, an alkylaryl group, for example a benzyl group, the —C(O)NH—R' group, R$^{IV}$ is a linear, cyclic or branched hydrocarbyl radical which also has further substitution, for example substitution by halogens, and has 1 to 50, preferably 9 to 45, more preferably 13 to 37, carbon atoms, R$^4$ may independently be R, R$^1$ and/or a functionalized organic, saturated or unsaturated radical having substitution by heteroatoms, selected from the group of the alkyl, aryl, chloroalkyl, chloroaryl, fluoroalkyl, cyanoalkyl, acryloyloxyaryl, acryloyloxyalkyl, methacryloyloxyalkyl, methacryloyloxypropyl and vinyl radical, with the proviso that at least one substituent from R$^1$, R$^2$ and R$^4$ is not R. The various monomer units in the structural units specified in the formulae (siloxane chains and/or polyoxyalkylene chain) may take the form of alternating blocks with any number of blocks in any sequence or be subject to a random distribution. The indices used in the formulae should be regarded as statistical averages.

The siloxanes of the formula (IX) can be prepared by known methods, for example the noble metal-catalyzed hydrosilylation reaction of compounds containing a double bond with corresponding hydrosiloxanes, as described, for example, in EP 1520870. The document EP 1520870 is hereby incorporated by reference and is considered to form part of the disclosure-content of the present invention.

Compounds having at least one double bond per molecule used may, for example, be α-olefins, vinyl polyoxyalkylenes and/or allyl polyoxyalkylenes. Preference is given to using vinyl polyoxyalkylenes and/or allyl polyoxyalkylenes. Particularly preferred vinyl polyoxyalkylenes are, for example, vinyl polyoxyalkylenes having a molar mass in the range from 100 g/mol to 8000 g/mol, which may be formed from the monomers propylene oxide, ethylene oxide, butylene oxide and/or styrene oxide in blocks or in random distribution, and which may either be hydroxy-functional or end-capped by a methyl ether function or an acetoxy function. Particularly preferred allyl polyoxyalkylenes are, for example, allyl polyoxyalkylenes having a molar mass in the range from 100 g/mol to 5000 g/mol, which may be formed from the monomers propylene oxide, ethylene oxide, butylene oxide and/or styrene oxide in blocks or in random distribution, and which may either be hydroxy-functional or end-capped by a methyl ether function or an acetoxy function. Particularly preferred compounds having at least one double bond per molecule are the α-olefins mentioned in the examples, allyl alcohol, 1-hexenol, vinyl polyoxyalkylenes and/or allyl polyoxyalkylenes, and also allyl glycidyl ether and vinylcyclohexene oxide.

Preference is given to using, in the context of the present invention (especially in the context of the inventive use), siloxanes of the formula (IX) in which a is independently 1 to 300, b is independently 1 to 50, c is independently 0 to 4, d is independently 0 to 4, with the proviso that, for each molecule of the formula (IX), the mean number $\Sigma d$ of T units and the mean number $\Sigma c$ of Q units per molecule is not greater than 20, the mean number $\Sigma a$ of D units per molecule is not greater than 1500 and the mean number $\Sigma b$ of R$^1$-bearing siloxy units per molecule is not greater than 50.

A particularly preferred embodiment of the present invention (especially in the context of the inventive use) uses siloxanes of the formula (IX) in which R$^1$ is independently an organic radical —CH$_2$—CH$_2$—CH$_2$—O—(CH$_2$—CH$_2$O—)$_x$—(CH$_2$—CH(R')O—)$_y$—R"   —CH$_2$—CH$_2$—O—(CH$_2$—CH$_2$O—)$_x$—(CH$_2$—CH(R')O—)$_y$—R" —CH$_2$—R$^{IV}$ in which x is 0 to 100, preferably >0, especially 1 to 50, and y is 0 to 100, preferably >0, especially 1 to 50, and R' are different and may each independently be methyl, ethyl and/or phenyl radicals. R" is independently a hydrogen radical or an alkyl group having 1 to 4 carbon atoms, a-C(O)—R'" group with R'"=alkyl radical, a —CH$_2$—O—R' group, an alkylaryl group, for example a benzyl group, the —C(O)NH—R' group, $R^{IV}$ is a linear, branched or cyclic, optionally substituted, for example halogen-substituted, hydrocarbyl radical having 1 to 50, preferably 9 to 45 and more preferably 13 to 37 carbon atoms.

A further preferred embodiment of the present invention (especially in the context of the inventive use), preferably for production of rigid foams, uses siloxanes of the formula (IX) in which $R^1$ is independently an organic radical selected from the group comprising —$CH_2$—$CH_2$—$CH_2$—O—($CH_2$—$CH_2$O—)$_x$—($CH_2$—CH(R')O—)$_y$—R" and/or —$CH_2$—$CH_2$—O—($CH_2$—$CH_2$O—)$_x$—($CH_2$—CH(R')O—)$_y$—R" and/or —$CH_2$—$R^{IV}$, in which x is 0 to 100, preferably >0, especially 1 to 50, y is 0 to 100, preferably >0, especially 1 to 50, R' is methyl and R" is independently a hydrogen radical or an alkyl group having 1 to 4 carbon atoms, a C(O)—R''' group with R'''=alkyl radical, a —CH2-O—R' group, an alkylaryl group, for example a benzyl group, the C(O)NH—R' group, where the molar proportion of oxyethylene units based on the total amount of oxyalkylene units accounts for at least 70% of the oxyalkylene units, i.e. x/(x+y)≥0.7. With this prerequisite, it is preferable that, in addition, the polyoxyalkylene chain bears a hydrogen at its end. With these prerequisites, a further preferred embodiment of the invention (especially in the context of the inventive use) uses siloxanes of the formula (IX) in which the oxyalkylene units present in the $R^1$ radical are exclusively oxyethylene units and, at the same time, the R" radical is not a hydrogen.

A further preferred embodiment of the present invention (especially in the context of the inventive use), preferably for production of flexible slabstock foams, uses siloxanes of the formula (IX) in which R1 is independently an organic radical selected from the group comprising —$CH_2$—$CH_2$—$CH_2$—O—($CH_2$—$CH_2$O—)$_x$—($CH_2$—CH(R')O—)$_y$—R" and/or —$CH_2$—$CH_2$—O—($CH_2$—$CH_2$O—)$_x$—($CH_2$—CH(R')O—)$_y$—R" and/or —$CH_2$—$R^{IV}$, in which x is 0 to 100, preferably >0, especially 1 to 50, y is 0 to 100, preferably >0, especially 1 to 50, R' is methyl and R" is independently a hydrogen radical or an alkyl group having 1 to 4 carbon atoms, a C(O)—R''' group with R'''=alkyl radical, a —CH2-O—R' group, an alkylaryl group, for example a benzyl group, the C(O)NH—R' group, where the molar proportion of oxyethylene units based on the total amount of oxyalkylene units accounts for not more than 60% of the oxyalkylene units, i.e. x/(x+y)<0.6.

A further preferred embodiment of the present invention (especially in the context of the inventive use) uses siloxanes of the formula (IX) in which the hydrosilylation is effected using, inter alia, olefins which result in $R^1$ consisting of $CH_2$—$R^{IV}$ to an extent of at least 10 mol %, preferably to an extent of at least 20 mol %, more preferably to an extent of at least 40 mol %, where $R^{IV}$ is a linear or branched hydrocarbon having 9 to 17 carbon atoms.

A further preferred embodiment of the present invention (especially in the context of the inventive use) uses siloxanes of the formula (IX) in which the terminal positions, also called the alpha and omega positions, in the siloxane are at least partly functionalized with $R^1$ radicals. In this case, at least 10 mol %, preferably at least 30 mol % and more preferably at least 50 mol % of the terminal positions are functionalized with $R^1$ radicals.

A particularly preferred embodiment of the invention (especially in the context of the inventive use) uses siloxanes of the formula (IX) in which a statistical average of not more than 50%, preferably not more than 45%, more preferably not more than 40%, of the total mean molar mass of the siloxane is accounted for by the cumulative molar mass of all the identical or different $R^1$ radicals in the siloxane.

A further preferred embodiment of the present invention (especially in the context of the inventive use) uses siloxanes of the formula (IX) in which the R radical is methyl and the structural elements having the index a are present in a greater number than the structural elements having the index b, in such a way that the quotient a/b is at least equal to seven, preferably greater than 10, more preferably greater than 12.

A further preferred embodiment of the present invention (especially in the context of the inventive use) uses siloxanes of the formula (IX) in which the oxyalkylene units present in the $R^1$ radical are exclusively oxyethylene units and, at the same time, the R" radical is not a hydrogen.

The siloxanes may also be used, in the context of the present invention (especially in the context of the inventive use), as part of compositions with different carrier media. Useful carrier media include, for example, glycols, for example monoethylene glycol (MEG), diethylene glycol (DEG), propylene glycol (PG) or dipropylene glycol (DPG), alkoxylates or oils of synthetic and/or natural origin.

Preferably, a sufficient amount of the siloxanes of the formula (IX) is added to the composition for production of polyurethane systems, preferably of polyurethane foams, that the proportion by mass of compounds of the formula (IX) in the finished polyurethane system, preferably the polyurethane foam, is from 0.01% to 10% by weight, preferably from 0.1% to 3% by weight.

The inventive nitrogen compounds of the formula (I), (II), (III), (IV), (V), (VI), (VII) and/or (VIII), or correspondingly quaternized and/or protonated compounds, are preferably used in the production of polyurethane systems, especially polyurethane foams.

It may be advantageous when the production of the polyurethane system involves producing and/or using a composition including at least one inventive nitrogen compound of the formula (I), (II), (III), (IV), (V), (VI), (VII) and/or (VIII), as defined above, and/or a corresponding quaternized and/or protonated compound, at least one polyol component, optionally at least one isocyanate component, and optionally one or more blowing agents, and reacting this composition. Particular preference is given to using those compositions which include the substances or components for production of polyurethanes, especially polyurethane foams, which have been described above in the context of use.

The invention further provides for the use of the above-described nitrogen compound of the formula (I), (II), (III), (IV), (V), (VI), (VII) and/or (VIII) or of a corresponding quaternized and/or protonated compound for production of low-emission polyurethanes, especially of low-emission polyurethane foams, advantageously in that they are low in emissions with respect to emissions of nitrogen compounds, as also previously called amine emissions, advantageously low in emissions with respect to emissions of dimethylformamide (DMF), and/or advantageously low in emissions with respect to aldehyde emissions, especially formaldehyde emissions. With regard to the expression "low emissions", reference is made to the preceding description and the elucidations therein, especially test methods. With regard to preferred configurations of this subject-matter, reference is likewise made to the above description, especially to the preferred embodiments mentioned.

The invention further provides for the use of the above-described nitrogen compound of the formula (I), (II), (III), (IV), (V), (VI), (VII) and/or (VIII) and/or a corresponding quaternized and/or protonated compound for production of low-odor polyurethanes, preferably of low-odor polyurethane foams, especially of low-odor flexible polyurethane foams. With regard to the expression "low odor", reference is made to the preceding description and the elucidations therein. With regard to preferred configurations of this subject-matter, reference is likewise made to the above description, especially to the preferred embodiments mentioned.

The invention further provides for the use of the above-described nitrogen compound of the formula (I), (II), (III), (IV), (V), (VI), (VII) and/or (VIII) and/or a corresponding quaternized and/or protonated compound for production of ageing-resistant polyurethane systems, especially polyurethane foams. With regard to the expression "ageing-resistant", reference is made to the preceding description and the elucidations and test methods therein. With regard to preferred configurations of this subject-matter, reference is likewise made to the above description, especially to the preferred embodiments mentioned.

The invention further provides for the use of the above-described nitrogen compound of the formula (I), (II), (III), (IV), (V), (VI), (VII) and/or (VIII) and/or a corresponding quaternized and/or protonated compound for production of discoloration-minimized polyurethane systems, especially polyurethane foams, preferably polyurethane for use in the automobile industry, especially in automobile interiors, for example as inner roof liners, interior door trim, die-cut sun visors, steering wheels and/or seat systems. "Discoloration-minimized" means that the polyurethane systems provided using inventive nitrogen-containing catalysts especially lead to lower discoloration of plastics, especially plastic covers, in automobile interiors than those polyurethane systems which are produced using conventional catalysts according to the prior art, especially noninventive amines, as can be shown, for example, by a PVC discoloration test. Here too, reference is made to the preceding description and the elucidations and test methods therein. With regard to preferred configurations of this subject-matter, reference is likewise made to the above description, especially to the preferred embodiments mentioned.

The invention further provides for the use of the above-described nitrogen compound of the formula (I), (II), (III), (IV), (V), (VI), (VII) and/or (VIII) and/or a corresponding quaternized and/or protonated compound for production of polyurethane systems having broad processing latitude, especially of semirigid polyurethane foams (open-cell rigid foams, especially for use as inner roof liner in automobile interiors). "Broad processing latitude" means that, in an advantageous manner, greater variation in the use concentration of the inventive nitrogen compounds is possible without any adverse effect on the desired material properties, for example the open-cell content of the foam or the three-dimensional weight distribution over the foam block, compared to comparable amine catalysts, or those typically used for such applications, according to the prior art. Here too, reference is made to the preceding description and the elucidations and test methods therein. With regard to preferred configurations of this subject-matter, reference is likewise made to the above description, especially to the preferred embodiments mentioned.

The invention further provides a composition comprising at least one polyol component, wherein the composition includes at least one nitrogen compound of the formula (I), (II), (III), (IV), (V), (VI), (VII) and/or (VIII) as defined and described above, and/or the corresponding quaternized and/or protonated compounds, wherein the composition preferably includes at least one isocyanate component, and wherein the nitrogen compound of the formula (I), (II), (III), (IV), (V), (VI), (VII) and/or (VIII) is preferably present in the form of a technical product mixture, as described above, and wherein the composition preferably comprises additional amine catalysts not of the formula (I), (II), (III), (IV), (V), (VI), (VII) and/or (VIII).

The molar ratio of the total amount of the nitrogen-containing catalysts, including the nitrogen compounds of the formula (I), (II), (III), (IV), (V), (VI), (VII) and/or (VIII), compared to the total amount of the groups in the polyol component that are reactive with isocyanates is preferably from $4 \times 10^{-4}:1$ to $0.2:1$.

It is preferable that the nitrogen compounds of the formula (I), (II), (III), (IV), (V), (VI), (VII) and/or (VIII) or corresponding quaternized and/or protonated compounds are used, in total, in a proportion by mass of 0.01 to 20 parts (pphp), preferably 0.01 to 5.00 parts and more preferably 0.02 to 3.00 parts, based on 100 parts (pphp) of polyol component.

The inventive composition may additionally include one or more blowing agents as described above. As well as or in place of blowing agents, the inventive composition may include further additions/auxiliaries or additives which are used in the production of polyurethane systems, preferably polyurethane foams. A selection of suitable auxiliaries/additions/additives, for example foam stabilizers or flame retardants, has already been described above for the production of the polyurethane systems, especially the polyurethane foams.

The processing of the inventive compositions to give polyurethane systems, especially polyurethane foams, can be effected by any methods known to the person skilled in the art, for example by manual mixing or preferably with the aid of foaming machines, especially low-pressure or high-pressure foaming machines. It is possible here to use batch processes, for example for production of molded foams, refrigerators, automobile seats and panels, or continuous processes, for example in the case of insulation boards, metal composite elements, slabstock foams or in the case of spraying processes.

It is possible to use all processes known to those skilled in the art for production of polyurethane foams. For example, the foaming operation can be effected either in the horizontal or in the vertical direction, in batchwise or continuous systems. It is likewise possible to utilize the compositions used in accordance with the invention for $CO_2$ technology. Use in low-pressure and high-pressure machines is possible, in which case the compositions can be metered directly into the mixing chamber or else are added upstream of the mixing chamber to one of the components which subsequently pass into the mixing chamber. The addition can also be effected in the raw material tank.

By means of the inventive use of nitrogen compounds of the formula (I), (II), (III), (IV), (V), (VI), (VII) and/or (VIII) and/or the corresponding quaternized and/or protonated compounds, it is possible to obtain the inventive polyurethane systems described hereinafter.

The present invention further provides a composition suitable for use in the production of polyurethanes, especially of polyurethane foams, comprising (a) at least one nitrogen compound of the formula (I), especially at least one nitrogen compound of the formula (II), (III), (IV), (V), (VI), (VII) and/or (VIII), more preferably at least one nitrogen compound of the formula (II) or (VI), advantageously in a total amount of ≥5% by weight, preferably 20%-95% by weight, especially 30%-70% by weight, (b) optionally 1-(3-aminopropyl)pyrrolidine, advantageously in an amount of ≥5% by weight, preferably 20%-95% by weight, especially 30%-70% by weight, (c) optionally 1-(2-aminoethyl)pyrrolidine, advantageously in an amount of ≥5% by weight, preferably 20%-95% by weight, especially 30%-70% by weight, (d) optionally 1-(2-hydroxyethyl)pyrrolidine, advantageously in an amount of ≥5% by weight, preferably 20%-95% by weight, especially 30%-70% by weight, (e) optionally 1-(3-hydroxypropyl)pyrrolidine, advantageously in an amount of ≥5% by weight, preferably 20%-95% by weight, especially 30%-70% by weight, (f) optionally trimethylenediamine, advantageously in an amount of ≥5% by weight, especially 20%-95% by weight, preferably 30%-70% by weight, (g) optionally ethylenediamine (EDA), advantageously in an amount of ≤95% by weight, especially 20%-90% by weight, preferably 30%-80% by weight, (h) optionally butane-1,4-diol, advantageously in an amount of ≤95% by weight, especially 20%-90% by weight, preferably 30%-80% by weight, (i) optionally monoethylene glycol (MEG), advantageously in an amount of ≤95% by weight, especially 20%-90% by weight, preferably 30%-80% by weight, (j) optionally diethylene glycol (DEG), advantageously in an amount of ≤95% by weight, especially 20%-90% by weight, preferably 30%-80% by weight, (k) optionally monoethanolamine (MEA), advantageously in an amount of ≤95% by weight, especially 20%-90% by weight, preferably 30%-80% by weight.

(l) optionally propylene glycol (PG), advantageously in an amount of ≤95% by weight, especially 20%-90% by weight, preferably 30%-80% by weight, (m) optionally dipropylene glycol (DPG), advantageously in an amount of ≤95% by weight, especially 20%-90% by weight, preferably 30%-80% by weight, and/or (n) optionally trimethylene glycol, butyl diglycol, neopentyl glycol, 2-methyl-1,3-propanediol, N,N-dimethylcyclohexylamine, N,N-dimethylaminopropylamine, triethylenediamine, 2,2,4-trimethyl-2-silamorpholine, N-ethyl-2,2-dimethyl-2-silamorpholine, N-(2-aminoethyl)morpholine, N-(2-hydroxyethyl)morpholine, N,N-dimethylaminoethanol, N,N-diethylaminoethanol, bis(2-dimethylaminoethyl ether), N,N-dimethylaminoethoxyethanol, N,N,N'-trimethyl-N'-(2-hydroxyethyl)bis(2-aminoethyl) ether, tris(dimethylaminopropyl)hexahydro-1,3,5-triazine, 1,8-diazabicyclo[5.4.0]undec-7-ene, 1,5-diazabicyclo[4.3.0]non-5-ene, 1,5,7-triazabicyclo[4.4.0]dec-5-ene, N-methyl-1,5,7-triazabicyclo[4.4.0]dec-5-ene, 1,4,6-triazabicyclo[3.3.0]oct-4-ene, 1,1,3,3-tetramethylguanidine and/or 2,4,6-tris(dimethylaminomethyl)phenol, advantageously in a total amount of ≤95% by weight, especially 20%-90% by weight, preferably 30%-80% by weight.

In the context of the aforementioned subject-matter of the present invention, particularly preferred compositions are those compositions in which at least one nitrogen compound of the formula (I), (II), (III), (IV), (V), (VI), (VII) and/or (VIII) and/or a corresponding quaternized and/or protonated compound is used in combination:

with b), with c), with d), with e), with f), with g), with h), with i), with j), with k), with l), with m), with n), with b) and h), with c) and h), with d) and h), with e) and h), with n) and h), with b) and i), with c) and i), with d) and i), with e) and i), with n) and i), with b) and j), with c) and j), with d) and j), with e) and j), with n) and j), with b) and l), with c) and l), with d) and l), with e) and l), with n) and l), with b) and m), with c) and m), with d) and m), with e) and m), with n) and m), with b) and d), with b), d) and h), with b), d) and i), with b), d) and j), with b), d) and l), with b), d) and m), with b) and n), with c) and n), with d) and n), with e) and n), with f) and n), with g) and n), with h) and n), with i) and n), with j) and n), with k) and n), with l) and n), with m) and n), with b), d) and n), with b), d), h) and n), with b), d), i) and n) with b), d), j) and n), with b), d), l) and n) or with b), d), m) and n).

The present invention therefore further provides a polyurethane system obtainable through a use as described above.

These inventive polyurethane systems are preferably polyurethane foams, more preferably rigid polyurethane foams, flexible polyurethane foams, viscoelastic foams, highly elastic foams, called "high-resilience foams" (HR), semirigid polyurethane foams, thermoformable polyurethane foams or integral foams. The term polyurethane should again be understood here as a generic term for any polymer prepared from di- or polyisocyanates and polyols or other isocyanate-reactive species, for example amines, though the urethane bond need not be the only or predominant type of bond. Polyisocyanurates and polyureas are also expressly included.

It is preferably a feature of the inventive polyurethane system, especially polyurethane foam, that it is a rigid polyurethane foam, a flexible polyurethane foam, a viscoelastic foam, a high-resilience (HR) foam, a semirigid polyurethane foam, a thermoformable polyurethane foam or an integral foam, preferably having a proportion by mass of nitrogen compounds of the formula (I), (II), (III), (IV), (V), (VI), (VII) and/or (VIII) and/or the corresponding quaternized and/or protonated compounds, or the residues obtained by conversion thereof, in the finished polyurethane foam of 0.005% to 10% by weight, preferably of 0.05% to 3% by weight, more preferably 0.1% to 1% by weight.

In a preferred embodiment, the inventive polyurethane foams, or those produced in accordance with the invention, are open-cell polyurethane foams, especially flexible polyurethane foams, more preferably hot-cure flexible polyurethane foams. In the context of the present invention, "open-cell" means that a foam has good air permeability (=porosity). The air permeability of the foam can be determined by dynamic pressure measurement on the foam. The dynamic pressure can be measured on the basis of EN 29053. If the dynamic pressure measured is reported in mm water column, open-cell polyurethane foams, especially flexible polyurethane foams, have a dynamic pressure of less than 100 mm, preferably ≤50 mm, water column, determined by the test method described in the examples.

A preferred composition for production of polyurethane or polyisocyanurate foam in the context of the present invention has a density of preferably 5 to 800, especially 5 to 300, more preferably 5 to 150 and especially preferably of 10 to 90 kg/m$^3$, and especially has the following composition:

| Component | Proportion by weight |
|---|---|
| Polyol | 100 |
| (Amine) catalyst | 0.05 to 5 |
| Tin catalyst | 0 to 5, preferably 0.001 to 2 |
| Potassium trimerization catalyst | 0 to 10 |
| Siloxane | 0.1 to 15, preferably 0.2 to 7 |

| Component | Proportion by weight |
| --- | --- |
| Water | 0 to <25, preferably 0.1 to 15 |
| Blowing agent | 0 to 130 |
| Flame retardant | 0 to 70 |
| Fillers | 0 to 150 |
| Further additives | 0 to 20 |
| Isocyanate index: | greater than 15 |

The invention further provides for the use of polyurethane systems, especially of polyurethane foams as described above, as refrigerator insulation, insulation panel, sandwich element, pipe insulation, spray foam, 1- and 1.5-pack canned foam, imitation wood, modelling foam, floral foam, packaging foam, mattress, furniture cushion, moldable foam for furniture, pillows, rebonded foam, sponge foam, automobile seat cushion, headrest, dashboard, automobile interior, automobile roof liner, sound absorption material, steering wheel, shoe sole, carpet backing foam, filter foam, sealing foam, sealant and adhesive, or for production of corresponding products.

The present invention is described in exemplary fashion in the examples cited below, without the invention, the scope of application of which results from the whole of the description and the claims, being limited to the embodiments mentioned in the examples.

EXAMPLES

Preparation of Inventive Nitrogen Compounds

The 1-(3-aminopropyl)pyrrolidine (CAS 23159-07-1) required for the synthesis of the inventive compounds of the formula (II) to (VII) was, as known from the prior art, prepared by the Michael addition of acrylonitrile onto pyrrolidine and subsequent hydrogenation of the nitrile formed and final fine distillation.

Synthesis Example 1

Preparation of 1-pyrrolidinepropanenitrile

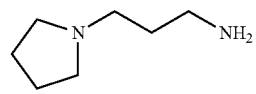

| Chemical | CAS | Supplier |
| --- | --- | --- |
| acrylonitrile, >99% | 107-13-1 | Sigma-Aldrich Chemie GmbH |
| pyrrolidine, 99% | 123-75-1 | ABCR |
| dichloromethane | 75-09-2 | Sigma-Aldrich Chemie GmbH |
| sodium hydroxide, ≥99%, p.a. | 1310-73-2 | Karl Roth GmbH |
| sodium chloride, ≥99.8%, extra fine | 7647-14-5 | Karl Roth GmbH |
| methanol, ≥99.8% | 67-56-1 | Sigma-Aldrich Chemie GmbH |

A 6 l five-neck flask equipped with dropping funnel, thermometer, precision glass stirrer and nitrogen feed is initially charged with 2224 ml of water at room temperature, and the reaction vessel is inertized. Then 861.2 ml (737.18 g, 10.37 mol) of pyrrolidine were added gradually, in the course of which the temperature rose to 35° C. The reaction apparatus was inertized again through the dropping funnel, and the latter was filled with 625 ml (500 g, 9.42 mol) of acrylonitrile. By means of a cooling bath, the amine solution was cooled down to −5° C., and then the addition of the acrylonitrile was commenced. Over the course of 5 hours, the rate of dropwise addition was adjusted in such a way that the reaction temperature did not exceed 5° C. The reaction mixture was allowed to warm up to room temperature and stirred for a further hour.

Then 2.1 l of a 33% by weight aqueous sodium hydroxide solution were added, whereupon a milky suspension formed. After the mixture had been decanted off into a separating funnel, the phases separated, and the turbid upper organic phase, still containing water, was separated. For better phase separation, 200 ml of dichloromethane and 50 ml of a cold-saturated sodium chloride solution were added. The upper, slightly opaque organic phase was dried over magnesium sulphate and the solvent was concentrated on a rotary evaporator. The fine distillation that followed gave 1.25 kg of a clear, pale yellow oil, the NMR spectroscopy analysis of which was in accordance with expectation. A GC analysis confirmed a purity of >95%.

Synthesis Example 2

Preparation of 1-(3-aminopropyl)pyrrolidine

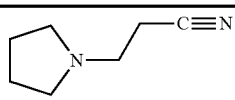

The subsequent hydrogenation of the above-prepared 1-pyrrolidinepropanenitrile was effected by means of Pd/Al$_2$O$_3$ (5% by weight), as described by Krupka and Jiri et al. in—"Hydrogenation of 3-(dimethylamino)propionitrile over palladium catalysts" (Czechoslovak Chemical Communications, 65 (11), 1805-1819; 2000). The resultant crude reaction mixture was admixed with Celite® filtering aid, filtered and rinsed through with methanol. The solvent was concentrated and the crude product was subjected to a fine distillation, wherein the main fraction distilled over at a top temperature of 90° C. in a membrane pump vacuum at 24 mbar. An alternative electrochemical method is described in SU1421738 (A1).

Synthesis Example 3

Preparation of a Compound of the Formula (II), Using the Example of the Compound of the Formula (IIa)

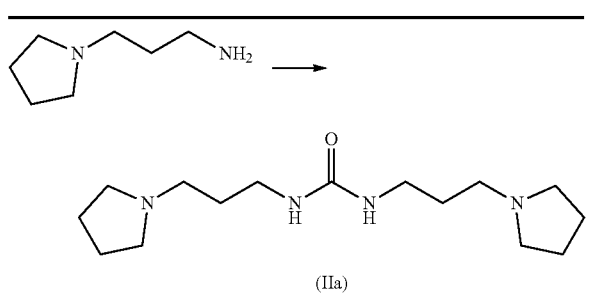

(IIa)

| Chemical | CAS | Supplier |
|---|---|---|
| urea, p.a. | 57-13-6 | Sigma-Aldrich Chemie GmbH |
| 1-(3-aminopropyl)pyrrolidine | 23159-07-1 | |

A four-neck flask equipped with precision glass stirrer, reflux condenser, temperature measurement probe and inert gas feed was initially charged with 19.82 g (0.33 mol) of urea, and 84.62 g (0.66 mol) of 1-(3-aminopropyl)pyrrolidine were added. After inertization of the reaction apparatus by means of nitrogen, the mixture was heated to 130° C., in the course of which the urea went into solution. A gentle nitrogen stream assured a constant inert gas atmosphere, and the progress of the reaction was recognized by a continuous loss of ammonia, which was detectable by means of indicator paper at the gas outlet. After a total reaction time of 32 hours, an oil-pump vacuum of >1 mbar was applied to the pale yellowish product mixture which was viscous at 130° C., and excess reactant and other volatile constituents were thus distilled off. After cooling, it was possible to obtain the desired product of the formula (IIa) as a white to pale beige, crystalline product. The 13C NMR analyses corresponded to expectation and confirmed that the desired product had formed.

Synthesis Example 4

Preparation of a Compound of the Formula (II), Using the Example of the Compound of the Formula (IIb)

(IIb)

| Chemical | CAS | Supplier |
|---|---|---|
| 1-methylurea | 598-50-5 | TCI Deutschland GmbH |
| 1-(3-aminopropyl)pyrrolidine | 23159-07-1 | |

A 250 ml four-neck flask equipped with precision glass stirrer, reflux condenser, temperature measurement probe and inert gas feed was initially charged with 40.75 g (0.55 mol) of 1-methylurea and 70.52 g (0.55 mol) of the previously prepared 1-(3-aminopropyl)pyrrolidine. Then the reaction apparatus was inertized with nitrogen and heated up to a reaction temperature of 110° C., in the course of which the methylurea melted in the temperature region of ~90° C., and a clear and colorless solution formed. A continuous loss of ammonia was observed, which was detectable by means of an indicator paper at the gas outlet. After a reaction time of 17 hours, the reaction temperature was increased to 130° C., and this was maintained for a further 17 hours. Since no significant loss of ammonia was detectable any longer, the mixture was left to cool to room temperature. It was thus possible to obtain 101 g of a pale yellow, highly viscous product of the formula (IIb), and the 13C NMR analysis confirmed product formation.

Synthesis Example 5

Preparation of a Compound of the Formula (II), Using the Example of the Compound of the Formula (IIc)

(IIc)

| Chemical | CAS | Supplier |
|---|---|---|
| 1-methylurea | 598-50-5 | TCI Deutschland GmbH |
| 1-(2-aminoethyl)pyrrolidine | 7154-73-6 | ABCR |

A 250 ml four-neck flask equipped with precision glass stirrer, reflux condenser, temperature measurement probe and inert gas feed was initially charged with 40.75 g (0.55 mol) of 1-methylurea and 62.80 g (0.55 mol) of 1-(2-aminoethyl)pyrrolidine. Then the reaction apparatus was inertized with nitrogen and heated up to a reaction temperature of 100° C., in the course of which the methylurea melted, and a clear and colorless solution formed. A continuous loss of ammonia was observed, which was detectable by means of an indicator paper at the gas outlet. After a reaction time of 32 hours, no significant loss of ammonia was detectable any longer and the reaction mixture was left to cool to room temperature. It was thus possible to obtain 92.2 g of a clear, pale brownish and highly viscous product of the formula (IIc), and the 13C NMR analysis confirmed product formation.

Synthesis Example 6

Preparation of a Compound of the Formula (III), Using the Example of the Compound of the Formula (IIIa)

(IIIa)

| Chemical | CAS | Supplier |
|---|---|---|
| ethylene carbonate, 98% | 96-49-1 | Sigma-Aldrich Chemie GmbH |

| | | |
|---|---|---|
| acetone, 99.6% | 67-64-1 | Acros Organics |
| 1-(3-aminopropyl)pyrrolidine | 23159-07-1 | |

A 250 ml four-neck flask equipped with precision glass stirrer, reflux condenser, temperature measurement probe and inert gas feed was initially charged with 51.29 g (0.4 mol) of 1-(3-aminopropyl)pyrrolidine, and the reaction apparatus was inertized with nitrogen and cooled down to 0° C. with a cooling bath. A dropping funnel was charged with 35.22 g (0.4 mol) of ethylene carbonate dissolved in 35 ml of demineralized water, which were then added dropwise within 4 hours in such a way that a reaction temperature of 5-10° C. was not exceeded. Then the reaction mixture was allowed to warm up to room temperature and stirred for a further five hours. The next day, about 100 ml of acetone were added to the product and the reaction mixture was transferred into a one-neck round-bottom flask. On a rotary evaporator, the solvents and all the volatile constituents were finally removed successively up to a final bath temperature of 60° C. and an oil-pump vacuum of <1 mbar. It was thus possible to obtain 84.8 g of a clear viscous product of the formula (IIIa). The $^{13}$C NMR spectroscopy analysis of the product was in accordance with expectation.

Synthesis Example 7

Preparation of a Compound of the Formula (III), Using the Example of the Compound of the Formula (IIIb)

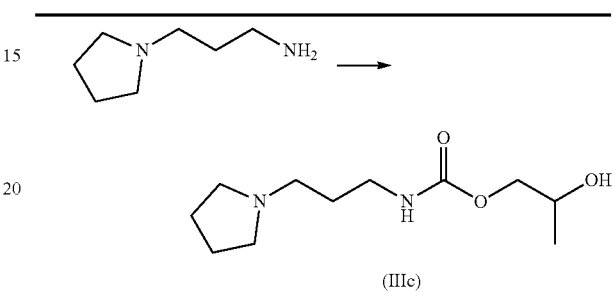

| Chemical | CAS | Supplier |
|---|---|---|
| ethylene carbonate, 98% | 96-49-1 | Sigma-Aldrich Chemie GmbH |
| acetone, 99.6% | 67-64-1 | Acros Organics |
| 1-(2-aminoethyl)pyrrolidine | 7154-73-6 | ABCR |

A 250 ml four-neck flask equipped with precision glass stirrer, reflux condenser, temperature measurement probe and inert gas feed was initially charged with 45.08 g (0.4 mol) of 1-(2-aminoethyl)pyrrolidine, and the reaction apparatus was inertized with nitrogen and cooled down to 0° C. with a cooling bath. A dropping funnel was charged with 35.22 g (0.4 mol) of ethylene carbonate dissolved in 35 ml of demineralized water, which were then added dropwise within 4 hours in such a way that a reaction temperature of 5-10° C. was not exceeded. Then the reaction mixture was allowed to warm up to room temperature and stirred for a further five hours. The next day, about 100 ml of acetone were added to the product and the reaction mixture was transferred into a one-neck round-bottom flask. On a rotary evaporator, the solvents and all the volatile constituents were finally removed successively up to a final bath temperature of 60° C. and an oil-pump vacuum of <1 mbar. It was thus possible to obtain 84.8 g of a clear viscous product of the formula (IIIb). The $^{13}$C NMR spectroscopy analysis of the product was in accordance with expectation.

Synthesis Example 8

Preparation of a Compound of the Formula (III), Using the Example of the Compound of the Formula (IIIc)

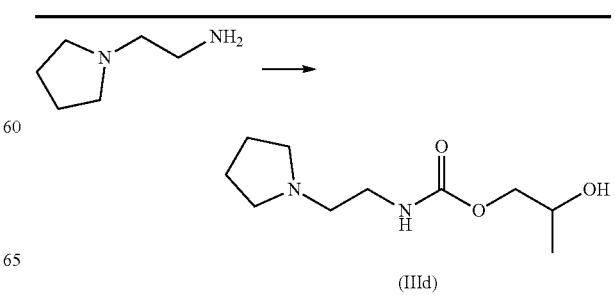

| Chemical | CAS | Supplier |
|---|---|---|
| propylene carbonate, 99% | 108-32-7 | Sigma-Aldrich Chemie GmbH |
| 1-(3-aminopropyl)pyrrolidine | 23159-07-1 | |

A 250 ml four-neck flask equipped with precision glass stirrer, reflux condenser, temperature measurement probe and inert gas feed was initially charged with 51.29 g (0.4 mol) of 1-(3-aminopropyl)pyrrolidine, and the reaction apparatus was inertized with nitrogen and cooled down to 0° C. with a cooling bath. By means of a dropping funnel, 40.84 g (0.4 mol) of propylene carbonate were then added dropwise within 4 hours in such a way that a reaction temperature of 5-10° C. was not exceeded. Then the reaction mixture was allowed to warm up to room temperature and stirred for a further five hours. The next day, the reaction mixture was transferred into a one-neck round-bottom flask, and all the volatile constituents were finally removed successively on a rotary evaporator up to a final bath temperature of 60° C. and an oil-pump vacuum of <1 mbar. It was thus possible to obtain 91 g of a clear viscous product of the formula (IIIc). The $^{13}$C NMR spectroscopy analysis of the product was in accordance with expectation.

Synthesis Example 9

Preparation of a Compound of the Formula (III), Using the Example of the Compound of the Formula (IIId)

-continued

| Chemical | CAS | Supplier |
|---|---|---|
| propylene carbonate, 99% | 108-32-7 | Sigma-Aldrich Chemie GmbH |
| 1-(2-aminoethyl)pyrrolidine | 7154-73-6 | ABCR |

A 250 ml four-neck flask equipped with precision glass stirrer, reflux condenser, temperature measurement probe and inert gas feed was initially charged with 45.68 g (0.4 mol) of 1-(2-aminoethyl)pyrrolidine, and the reaction apparatus was inertized with nitrogen and cooled down to 0° C. with a cooling bath. By means of a dropping funnel, 40.84 g (0.4 mol) of propylene carbonate were then added dropwise within 4 hours in such a way that a reaction temperature of 5-10° C. was not exceeded. Then the reaction mixture was allowed to warm up to room temperature and stirred for a further five hours. The next day, the reaction mixture was transferred into a one-neck round-bottom flask, and all the volatile constituents were finally removed successively on a rotary evaporator up to a final bath temperature of 60° C. and an oil-pump vacuum of <1 mbar. It was thus possible to obtain 85.6 g of a clear, pale yellowish and viscous product of the formula (IIId). The $^{13}$C NMR spectroscopy analysis of the product was in accordance with expectation.

Synthesis Example 10

Preparation of a Compound of the Formula (IV), Using the Example of the Compound of the Formula (IVa)

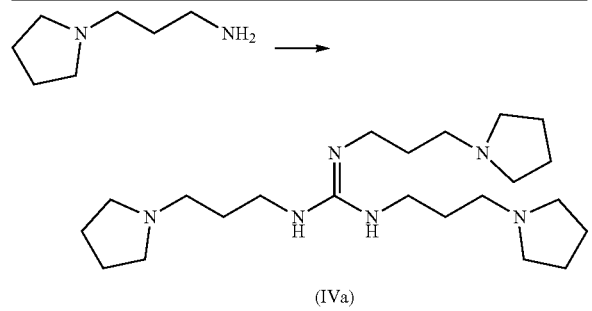

(IVa)

| Chemical | CAS | Supplier |
|---|---|---|
| guanidine hydrochloride, >99% | 50-01-1 | Sigma-Aldrich Chemie GmbH |
| 1-(3-aminopropyl)pyrrolidine | 23159-07-1 | |
| sodium methoxide | 124-41-4 | ABCR |
| methanol | 67-56-1 | Sigma-Aldrich Chemie GmbH |

A 250 ml four-neck flask equipped with reflux condenser, precision glass stirrer, internal thermometer and argon inlet was initially charged with 114.19 g (1 mol) of 1-(3-aminopropyl)pyrrolidine under inert conditions, and 31.84 g (0.33 mol) of guanidine hydrochloride were added. The reaction mixture thus produced was heated up to 110° C., and a gentle vacuum was applied by means of a membrane pump in order to facilitate the departure of ammonia. The color of the product changed to red-brown within a few minutes. After a total reaction time of 35 hours, all the volatile constituents were removed at 95-100° C. in an oil-pump vacuum (<1 mbar). In the course of cooling to room temperature, the red-brown product crystallized, but exhibited good solubility in standard laboratory solvents. The 1H/13C NMR spectra confirmed product formation and corresponded to expectation.

In order to obtain the analogous free guanidine base, an aliquot of the above product was dissolved in 40% by weight solution in methanol, and a stoichiometric amount of sodium methoxide was added. After stirring at room temperature overnight, turbidity was observed, and the solvent was removed on a rotary evaporator at 80° C. and a pressure of 1 mbar, resulting in precipitation of sodium chloride. After filtration by means of a pressurized filter press, it was possible to obtain the free guanidine base of the formula (IVa) as a brown oil.

Synthesis Example 11

Preparation of a Compound of the Formula (IV), Using the Example of the Compound of the Formula (IVb)

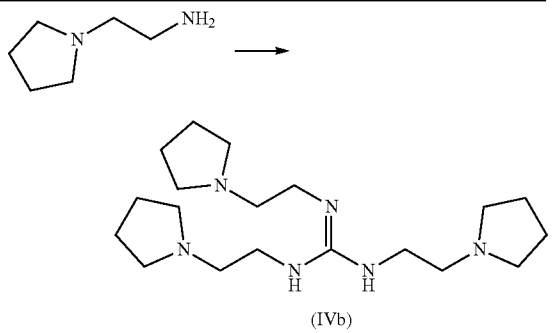

(IVb)

| Chemical | CAS | Supplier |
|---|---|---|
| guanidine hydrochloride, >99% | 50-01-1 | Sigma-Aldrich Chemie GmbH |
| 1-(2-aminoethyl)pyrrolidine | 7154-73-6 | ABCR |
| sodium methoxide | 124-41-4 | ABCR |
| methanol | 67-56-1 | Sigma-Aldrich Chemie GmbH |

A 250 ml four-neck flask equipped with reflux condenser, precision glass stirrer, internal thermometer and argon inlet was initially charged with 76.0 g (0.66 mol) of 1-(2-aminoethyl)pyrrolidine under inert conditions, and 15.92 g (0.166 mol) of guanidine hydrochloride were added. The reaction mixture thus produced was heated up to 110° C., and a gentle vacuum was applied by means of a membrane pump in order to facilitate the departure of ammonia. The color of the product changed to red-brown within a few minutes. After a total reaction time of 35 hours, the excess equivalent of 1-(2-aminoethyl)pyrrolidine and all the other volatile constituents were removed at 95-100° C. in an oil-pump vacuum (<1 mbar). In the course of cooling to room temperature, the red-brown product crystallized, but exhibited good solubility in standard laboratory solvents. The 1H/13C NMR spectra confirmed product formation and corresponded to expectation.

In order to obtain the analogous free guanidine base, an aliquot of the above product was dissolved in 40% by weight solution in methanol, and a stoichiometric amount of sodium methoxide was added. After stirring at room temperature overnight, turbidity was observed, and the solvent was removed on a rotary evaporator at 80° C. and a pressure of 1 mbar, resulting in precipitation of sodium chloride. After filtration by means of a pressurized filter press, it was possible to obtain the free guanidine base of the formula (IVb) as a brown oil.

Synthesis Example 12

Preparation of a Compound of the Formula (V), Using the Example of the Compound of the Formula (Va)

(Va)

| Chemical | CAS | Supplier |
|---|---|---|
| caprolactone, 97% | 502-44-3 | Sigma-Aldrich Chemie GmbH |
| 1-(3-aminopropyl)pyrrolidine | 23159-07-1 | |

A 1000 ml four-neck flask equipped with reflux condenser, precision glass stirrer, internal thermometer and argon inlet is initially charged under inert conditions with 256.43 g (2 mol) of 1-(3-aminopropyl)pyrrolidine and 228.28 g (2 mol) of ε-caprolactone. The reaction mixture thus produced was heated to 150° C. for four hours. After the reaction had ended, the mixture was fractionated using a short cold finger in an oil-pump vacuum ($5 \cdot 10^{-2}$ mbar), and it was possible to obtain a main fraction of 241 g of the product with ~50% yield. The 1H/13C NMR spectra of the main fraction confirmed that the product of the formula (Va) had been formed and corresponded to expectation.

Synthesis Example 13

Preparation of a Compound of the Formula (VI), Using the Example of the Compound of the Formula (VIa)

(VIa)

| Chemical | CAS | Supplier |
|---|---|---|
| 1,6-dichlorohexane, 98% | 2163-00-0 | Sigma-Aldrich Chemie GmbH |
| triethylamine, 99% | 121-44-8 | ABCR |
| toluene, 99.5%, ACS | 108-88-3 | Acros Organics |
| sodium hydroxide, ≥99%, p.a. | 1310-73-2 | Karl Roth GmbH |
| diethyl ether, 99% | 60-29-7 | Sigma-Aldrich Chemie GmbH |

A 1 l four-neck flask equipped with precision glass stirrer, reflux condenser, temperature measurement probe and inert gas feed was initially charged with 242.9 g (2.4 mol) of triethylamine and 50 g of toluene. Then the reaction apparatus was inertized with nitrogen, and 170.7 g (2.4 mol) of pyrrolidine were added at room temperature, whereupon the temperature rose to 35° C. Subsequently, the mixture was heated to pyrrolidine reflux at 77° C. and an amount of 93.4 g (0.6 mol) of 1,6-dichlorohexane was added by means of a dropping funnel within 10 minutes. The mixture was stirred at 86° C. for a further 16 hours and then a solution of 48.2 g of sodium hydroxide in 250 ml of water was added. The now biphasic reaction mixture was transferred into a separating funnel, the organic phase was removed and the aqueous phase was extracted 2× with 100 ml each time of diethyl ether. The combined organic phases were concentrated on a rotary evaporator at 80° C. and 30 mbar, and the crude product was subjected to a fractional distillation. At a top temperature of 125° C. and oil-pump vacuum 3 mbar, it was possible to obtain 44.1 g of a clear colorless fraction of the product of the formula (VIa), which had a purity of 97.3% by GC analysis.

Rigid Foam—Foaming Examples

Example 1

Production of Rigid Polyurethane Foams, for Example for Use in the Insulation of Cooling Units For the performance testing of the inventive nitrogen compounds, the foam formulation specified in Table 1 was used.

TABLE 1

Formulation 1 for rigid foam applications

| Formulation 1 | Parts by mass (pphp) |
|---|---|
| Polyol 1 [1] | 100 parts |
| Water | 2.60 parts |
| Cyclopentane | 13.1 parts |
| Amine | 0.80 or 1.50 parts (see Table 2) |
| TEGOSTAB ® B 8460 [2] | 1.50 parts |
| Desmodur ® 44V20L [3] | 198.5 parts |

[1] Polyol 1: sorbitol/glycerol-based polyether polyol having an OH number of 471 mg KOH/g.
[2] Polyether-modified polysiloxane.
[3] Polymeric MDI from Bayer, 200 mPa · s, 31.5% NCO, functionality 2.7.

The foams were produced by manual mixing. The formulations as specified in Table 1 were used with various nitrogen-containing catalysts (amines). For this purpose, polyol 1, conventional or inventive nitrogen-containing catalyst (amine), water, foam stabilizer and blowing agent were weighed into a cup and mixed with a disc stirrer of diameter 6 cm at 1000 rpm for 30 seconds. The blowing agent quantity which had evaporated during the mixing operation was determined by reweighing and replenished. Now the isocyanate (MDI) was added, and the reaction mixture was stirred with the stirrer described at 3000 rpm for 5 s and transferred immediately into a paper-lined box (base area 27 cm×14 cm and height 14 cm). To assess the catalytic properties, the following characteristic parameters were determined: cream time, gel time (fiber time), rise time and tack-free time.

The results of the assessment of the catalytic properties of the inventive nitrogen compounds of the formulae (II), (III), (IV), (V) and (VI) are compiled in Table 2. Comparative catalysts according to the prior art used were N,N-dimethylcyclohexylamine (DMCHA), dimethylaminoethoxyethanol (DMEE) and pentamethyldiethylenetriamine (PMDETA).

TABLE 2

Results of the foaming operations on formulation 1 (Table 1)

| Amine | Cream time [s][3] | Gel time [s][3] | Rise time [s][3] | Tack-free time [s][3] |
|---|---|---|---|---|
| DMCHA[1] | 38 | 137 | 298 | 310 |
| DMEE[1] | 30 | 150 | 272 | 308 |
| PMDETA[2] | 15 | 128 | 199 | 224 |
| FORMULA (IIa)[1] | 100 | 375 | 440 | 478 |
| FORMULA (IIb)[1] | 55 | 225 | 315 | 408 |
| FORMULA (IIc)[1] | 50 | 210 | 315 | 405 |
| FORMULA (IIIa)[1] | 65 | 275 | 350 | 431 |
| FORMULA (IIIb)[1] | 90 | 325 | 417 | 444 |
| FORMULA (IIIc)[1] | 80 | 280 | 345 | 428 |
| FORMULA (IIId)[1] | 85 | 315 | 405 | 445 |
| FORMULA (IVa)[1] | 103 | 390 | 435 | 475 |
| FORMULA (IVb)[1] | 105 | 397 | 438 | 460 |
| FORMULA (Va)[1] | 79 | 277 | 347 | 431 |
| FORMULA (VIa)[1] | 35 | 120 | 155 | 205 |

[1]1.50 parts catalyst used.
[2]1.50 parts catalyst used.
[3]Times reported in seconds [s].

As can be inferred from Table 2, the inventive nitrogen compounds of the formulae (II), (III), (IV), (V) and (VI) show a moderate to very good catalytic activity and selectivity in the rigid foam, in some cases comparable to DMCHA and in some cases even better than DMEE. The compound of the formula (VIa) is even a very selective blowing catalyst which is very much more vigorous in terms of activity than DMEE and has a similar selectivity profile to PMDETA.

Flexible Foam—Performance Tests

Physical properties of the flexible polyurethane foams:

The flexible polyurethane foams produced were assessed using the following physical properties:

a) Foam settling after the end of the rise phase (=fall-back): The fall-back, or the further rise, is found from the difference in the foam height after direct blow-off and after 3 minutes after foam blow-off. The foam height is measured at the maximum in the middle of the foam crest by means of a needle secured to a centimeter scale. A negative value here describes the settling of the foam after blow-off; a positive value correspondingly describes the further rise of the foam.

b) Foam height: The final height of the foam is determined by subtracting the fall-back from or adding the further rise to the foam height after blow-off. Foam height is reported in centimeters (cm).

c) Density: The determination is effected, as described in ASTM D 3574-11 under Test A, by measuring the core density. Density is reported in kg/m$^3$.

d) Porosity: The air permeability of the foam was determined by dynamic pressure measurement on the foam. The dynamic pressure measured is reported in mm water column, and lower dynamic pressure values characterize a more open foam. The values were measured in the range from 0 to 300 mm.

The dynamic pressure was measured by means of an apparatus comprising a nitrogen source, a reducing valve with manometer, a screw-thread flow regulator, a wash bottle, a flow meter, a T-piece, a nozzle head and a scaled glass tube filled with water. The nozzle head has an edge length of 100×100 mm, a weight of 800 g, a clear width of the exit orifice of 5 mm, a clear width of the lower applicator ring of 20 mm and an external diameter of the lower applicator ring of 30 mm.

The measurement is effected by adjusting the nitrogen supply pressure to 1 bar with the reducing valve and adjusting the flow rate to 480 l/h. The amount of water in the scaled glass tube is adjusted such that no pressure differential is built up and none can be read off. For the analysis of the test specimen having dimensions of 250×250×50 mm, the nozzle head is placed onto the corners of the test specimen, flush with the edges, and once onto the (estimated) middle of the test specimen (in each case on the side with the greatest surface area). The result is read off when a constant dynamic pressure has been established.

Evaluation is effected by forming the average of the five measurements obtained.

e) Indentation hardness CLD, 40% to DIN EN ISO 3386. The measurements are reported in kilopascal (kPa).

Measurement of foam emissions (VOC and fog value) based on test method VDA 278 in the version dated October 2011:

The method serves to determine emissions from nonmetallic materials used for molded parts in motor vehicles. The emission of volatile organic compounds (VOC value, 30 minutes at 90° C.) and the proportion of condensable substances (fog value, 60 minutes at 120° C.), especially of the catalysis-related emissions, the emissions of the individual constituents of inventive catalyst combinations or the breakdown or conversion products thereof, were determined based on test method VDA 278 in the version dated October 2011. There follows a description of the procedure for the corresponding thermal desorption with subsequent gas chromatography-mass spectrometry coupling (GC-MS).

a) Equipment: The thermal desorption was conducted with a "TDS2" thermal desorber with autosampler from Gerstel, Mülheim, in conjunction with an Agilent 7890/5975 GC/MSD system.

b) The measurement conditions for VOC analyses are stated in Tables 3 and 4.

TABLE 3

Thermal desorption analysis parameters for the VOC analysis run

| Thermal desorption | Gerstel TDS2 |
|---|---|
| Desorption temperature | 90° C. |
| Desorption time | 30 min |
| Flow rate | 65 ml/min |
| Transfer line | 280° C. |
| Cryofocusing | KAS 4 |
| Liner | glass evaporator tube with silanized glass wool |
| Temperature | −150° C. |

TABLE 4

Gas chromatography-mass spectrometry analysis parameters for the VOC analysis run

| GC | capillary - GC Agilent 7890 |
|---|---|
| Injector | PTV split 1:50 |
| Temperature programme | −150° C.; 1 min; ↗ 10° C./s; 280° C. |
| Column | Agilent 19091B-115, Ultra 2, 50 m * 0.32 mm FT 0.5 μm |

TABLE 4-continued

Gas chromatography-mass spectrometry analysis
parameters for the VOC analysis run

| | |
|---|---|
| Flow rate | 1.3 ml/min const. Flow |
| Temperature programme | 50° C.; 2 min; ↗3° C./min; 92° C.; ↗5° C./min; 160° C.; ↗10° C./min; 280° C., 20 min |
| Detector | Agilent MSD 5975 |
| Mode | Scan 29-350 amu 2.3 scans/sec |
| Evaluation | Evaluation of the total ion current chromatogram by calculation as toluene equivalent | c) Calibration: For calibration, 2 µl of a mixture of toluene and hexadecane in methanol (0.125 mg/ml of each) were introduced into a cleaned adsorption tube filled with Tenax® TA (mesh 35/60) and analyzed (desorption 5 min; 280° C.).

d) Tenax TA is a porous polymer resin based on 2,6-diphenylene oxide, obtainable, for example, from Scientific Instrument Services, 1027 Old York Rd., Ringoes, N.J. 08551.

e) Sample preparation for the VOC analysis: 15 mg of foam were positioned in three sample portions in a thermal desorption tube. In doing so, it was ensured that the foam was not compressed.

f) Sample preparation for the fog analysis: The same foam sample was used as for the VOC analysis. With regard to the measurement arrangement, the VOC analysis was always conducted first and the fog analysis thereafter, ensuring a constant separation between each of the corresponding VOC and fog analyses by means of an autosampler system.

g) The measurement conditions for fog analyses are stated in Tables 5 and 6.

TABLE 5

Thermal desorption analysis parameters for the fog analysis run

| | |
|---|---|
| Thermal desorption | Gerstel TDS2 |
| Desorption temperature | 120° C. |
| Desorption time | 60 min |
| Flow rate | 65 ml/min |
| Transfer line | 280° C. |
| Cryofocusing | KAS 4 |
| Liner | glass evaporator tube with silanized glass wool |
| Temperature | −150° C. |

TABLE 6

Gas chromatography-mass spectrometry analysis
parameters for the fog analysis run

| | |
|---|---|
| GC | capillary - GC Agilent 7890 |
| Injector | PTV split 1:50 |
| Temperature programme | −150° C.; 1 min; ↗10° C./s; 280° C. |
| Column | Agilent 19091B-115, Ultra 2, 50 m * 0.32 mm FT 0.5 µm |
| Flow rate | 1.3 ml/min const. Flow |
| Temperature programme | 50° C.; 2 min; ↗25° C./min; 160° C.; ↗10° C./min; 280° C.; 20 min |
| Detector | Agilent MSD 5975 |
| Mode | Scan 29-450 amu 2.3 scans/sec |
| Evaluation | Evaluation of the total ion current chromatogram by calculation as hexadecane equivalent | h) Calibration: For calibration, 2 µl of a mixture of toluene and hexadecane in methanol (0.125 mg/ml of each) were introduced into a cleaned adsorption tube filled with Tenax® TA (mesh 35/60) and analyzed (desorption 5 min; 280° C.).

Determination of room temperature emissions by the test chamber test:

The emission, especially the catalysis-related emissions, the emissions of the individual constituents of inventive catalyst combinations or the breakdown or conversion products thereof were determined at room temperature based on DIN method DIN EN ISO 16000-9:2008-04. Sampling was affected after 24 hours. For this purpose, 2 l of the test chamber atmosphere were passed through an adsorption tube filled with Tenax® TA (mesh35/60) at a flow rate of 100 ml/min. There follows a description of the procedure for the thermal desorption with subsequent gas chromatography-mass spectrometry coupling (GC-MS).

a) Equipment: The thermal desorption was conducted with a "TDS2" thermal desorber with autosampler from Gerstel, Mülheim, in conjunction with an Agilent 7890/5975 GC/MSD system.

b) The measurement conditions are stated in Tables 7 and 8.

TABLE 7

Analysis parameters for thermal desorption
for test chamber analysis

| | |
|---|---|
| Thermal desorption | Gerstel TDS2 |
| Desorption temperature | 280° C. |
| Desorption time | 5 min |
| Flow rate | 65 ml/min |
| Transfer line | 280° C. |
| Cryofocusing | KAS 4 |
| Liner | glass evaporator tube with silanized glass wool |
| Temperature | −150° C. |

TABLE 8

Gas chromatography-mass spectrometry analysis
parameters for test chamber analysis

| | |
|---|---|
| GC | capillary - GC Agilent 7890 |
| Temperature programme | −150° C.; 1 min; ↗10° C./s; 280° C. |
| Column | Agilent 19091B-115, Ultra 2, 50 m * 0.32 mm FT 0.5 µm |
| Flow rate | 1.3 ml/min const. Flow |
| Temperature programme | 50° C.; 2 min; ↗3° C./min; 92° C.; ↗5° C./min; 160° C.; ↗10° C./min; 280° C., 20 min |
| Detector | Agilent MSD 5975 |
| Evaluation | Evaluation of the total ion current chromatogram by calculation as toluene equivalent | c) For calibration, 2 µl of a mixture of toluene and hexadecane in methanol (0.125 mg/ml of each) were introduced into a cleaned adsorption tube filled with Tenax® TA (mesh35/60) and analyzed (desorption 5 min; 280° C.).

Flexible Foam—Foaming Examples

Example 2

Production of Flexible Polyurethane Foams
(Flexible Slabstock Foam)

For the performance testing of the inventive nitrogen compounds, the foam formulation specified in Table 9 was used.

TABLE 9

Formulation 2 for flexible slabstock foam applications

| Formulation 2 | Parts by mass (pphp) |
|---|---|
| Polyol 1 [1] | 100 parts |
| Water | 3.00 parts |
| Tin catalyst[2] | 0.20 parts |
| Amine | 0.20 parts |
| TEGOSTAB ® BF 2370[3] | 0.80 parts |
| Desmodur ® T 80[4] | 38.1 parts |

[1] Polyol 1: glycerol-based polyether polyol having an OH number of 48 mg KOH/g.
[2] KOSMOS ® 29, available from Evonik Industries: tin(II) salt of 2-ethylhexanoic acid.
[3] Polyether-modified polysiloxane.
[4] Tolylene diisocyanate T 80 (80% 2,4 isomer, 20% 2,6 isomer) from Bayer, 3 mPa·s, 48% NCO, functionality 2.

In the foaming operation, 500 g of polyol were used; the other formulation constituents were adjusted correspondingly. In this context, for example, 1.00 part of a component meant 1.00 g of a substance per 100 g of polyol.

The foams were produced by manual mixing. The formulations as specified in Table 9 were used with various nitrogen-containing catalysts (amines). For this purpose, polyol, conventional or inventive nitrogen-containing catalyst (amine), tin catalyst, water and foam stabilizer were weighed into a cup and mixed at 1000 rpm for 60 seconds. After the isocyanate (TDI) had been added, the reaction mixture was stirred at 2500 rpm for 7 s and transferred immediately into a paper-lined box (base area 27 cm×27 cm and height 27 cm). To assess the catalytic properties, the following characteristic parameters were determined: cream time, rise time, rise height, blow-off intensity and settling of the foam after the end of the rise phase (=fall-back).

Defined foam pieces were cut out of the resulting foam blocks and were analyzed further. The following physical properties were determined using the specimens: density, porosity (=air permeability) and indentation hardness CLD (40%).

The results of the assessment of the catalytic properties of the inventive nitrogen compounds of the formulae (II), (III), (IV), (V) and (VI) and the physical properties of the resulting flexible slabstock foams are compiled in Table 10. Comparative catalysts used according to the prior art were triethylenediamine, 33% by weight solution in dipropylene glycol (TEGOAMIN® 33, available from Evonik Industries), N,N-dimethylethanolamine (TEGOAMIN® DMEA, available from Evonik Industries), 1,1'-{[3-(dimethylamino)propyl]imino}bis-2-propanol (TEGOAMIN® ZE 1, available from Evonik Industries), bis(2-dimethylaminoethyl) ether), 70% by weight solution in dipropylene glycol (TEGOAMIN® BDE, available from Evonik Industries) and N,N,N'-trimethyl-N'-(2-hydroxyethyl)bis(2-aminoethyl) ether (Jeffcat® ZF-10, available from Huntsman). 0.20 pphp (=parts by weight based on 100 parts by weight of polyol) of amine was used in each case.

TABLE 10

Results of the foaming operations on formulation 2 (Table 9)

| Amine | Rise time [s] | Fall-back [cm] | Height [cm] | Density [kg/m³] | Porosity [mm][1] | CLD 40% [kPa] |
|---|---|---|---|---|---|---|
| TEGOAMIN ® 33 | 118 | 0.1 | 28.7 | 31.8 | 24 | 4.4 |
| TEGOAMIN ® ZE 1 | 143 | 0.2 | 28.2 | 31.9 | 24 | 4.3 |
| TEGOAMIN ® DMEA | 140 | 0.1 | 28.0 | 31.2 | 14 | 3.7 |
| TEGOAMIN ® BDE | 91 | 0.8 | 28.8 | 30.8 | 8 | 3.3 |
| Jeffcat ® ZF-10 | 108 | 0.7 | 28.9 | 30.7 | 9 | 3.4 |
| FORMULA (IIa) | 124 | 0.1 | 28.5 | 31.5 | 22 | 4.1 |
| FORMULA (IIb) | 127 | 0.2 | 28.6 | 31.3 | 23 | 4.0 |
| FORMULA (IIc) | 131 | 0.1 | 28.4 | 31.0 | 27 | 3.9 |
| FORMULA (IIIa) | 140 | 0.2 | 28.4 | 31.7 | 23 | 3.9 |
| FORMULA (IIIb) | 140 | 0.1 | 28.7 | 31.5 | 21 | 4.0 |
| FORMULA (IVa) | 138 | 0.2 | 28.5 | 31.2 | 28 | 4.3 |
| FORMULA (Va) | 143 | 0.1 | 27.6 | 31.3 | 26 | 3.9 |
| FORMULA (VIa) | 118 | 0.5 | 28.8 | 30.9 | 12 | 3.6 |

[1] = (dynamic pressure in mm water column).

As can be inferred from Table 10, the inventive nitrogen compounds of the formulae (II), (III), (IV), (V) and (VI) exhibit moderate to good catalytic activity in a flexible foam. In terms of their catalytic profile and their selectivity, all the compounds of the formulae (II), (III), (IV) and (V) examined can be classified as slightly gel-selective catalysts and, in this regard, are all within a range similar to TEGOAMIN ZE 1 or TEGOAMIN® DMEA. The compounds of the formulae (IIa), (IIb), (IIc) and (VIa) are actually within the range of TEGOAMIN® 33 in terms of their rise profile. The compound of the formula (VIa) in particular has excellent catalytic activity, but the comparatively large fall-back and the somewhat lower CLD value are an indication that structure (VIa) is a more blowing-selective catalyst than TEGOAMIN® 33.

Example 3

Emissions from Flexible Slabstock Polyurethane Foams

In order to study the influence of the inventive nitrogen compounds on foam emissions, the foam formulation specified in Table 11 containing a low-emission polyol and a low-emission tin catalyst was used for the performance testing of flexible slabstock foams.

TABLE 11

Formulation 3, foam emissions in flexible slabstock foam applications

| Formulation 3 | Parts by mass (pphp) |
|---|---|
| Polyol 1 [1] | 100 parts |
| Water | 3.00 parts |
| Tin catalyst[2] | 0.60 parts |
| Amine | 0.15 parts |
| TEGOSTAB ® BF 2370[3] | 0.80 parts |
| Desmodur ® T 80[4] | 41.6 parts |

[1] Polyol 1: low-emission glycerol-based polyether polyol having an OH number of 56 mg KOH/g.
[2] KOSMOS ® EF, available from Evonik Industries: tin(II) salt of ricinoleic acid.
[3] Polyether-modified polysiloxane.
[4] Tolylene diisocyanate T 80 (80% 2,4 isomer, 20% 2,6 isomer) from Bayer, 3 mPa·s, 48% NCO, functionality 2.

In the foaming operation, 500 g of polyol were used; the other formulation constituents were adjusted correspondingly. In this context, for example, 1.00 part of a component meant 1.00 g of a substance per 100 g of polyol.

The foams were produced by manual mixing. The formulations as specified in Table 11 were used with various nitrogen-containing catalysts (amines). For this purpose, low-emission polyol, conventional or inventive nitrogen-containing catalyst (amine), low-emission tin catalyst, water and foam stabilizer were weighed into a cup and mixed at 1000 rpm for 60 seconds. After the isocyanate (TDI) had been added, the reaction mixture was stirred at 2500 rpm for 7 s and transferred immediately into a paper-lined box (base area 27 cm×27 cm and height 27 cm) and the resulting foam, after blow-off, was sealed airtight with polyethylene film. After a curing phase of 24 hours, a defined foam cube (7 cm×7 cm×7 cm) was cut out of the resulting foam block, which was fully encased with aluminum foil and additionally sealed with polyethylene film.

The emission characteristics of the above-described foams were subsequently examined at room temperature by the test chamber test based on the DIN method DIN EN ISO 16000-9:2008-04 as described above. The results are given in Table 12.

TABLE 12

Emissions from the flexible slabstock foams according to formulation 3 (Table 11)

| Amine | Content of volatile organic compounds by the test chamber test (TCT) | |
| --- | --- | --- |
| | $TCT_{tot}$[1] $[\mu g/m^3]$ | $TCT_{amine}$[1] $[\mu g/m^3]$ |
| TEGOAMIN ® 33 | 92 | 64 |
| TEGOAMIN ® ZE 1 | <20 | <10 |
| TEGOAMIN ® DMEA | 28 | <10 |
| TEGOAMIN ® BDE | 340 | 293 |
| Jeffcat ® ZF-10 | <20 | <10 |
| FORMULA (IIa) | <20 | <10 |
| FORMULA (IIb) | <20 | <10 |
| FORMULA (IIc) | <20 | <10 |
| FORMULA (IIIa) | <20 | <10 |
| FORMULA (IIIb) | <20 | <10 |
| FORMULA (IVa) | <20 | <10 |
| FORMULA (Va) | <20 | <10 |
| FORMULA (VIa) | <20 | <10 |

[1] $TCT_{tot}$ = total emissions; $TCT_{amine}$ = amine emissions of all volatile organic compounds in the test chamber test.

Table 12 shows that it is possible to distinctly reduce amine emissions in the test chamber test when using the inventive nitrogen compounds of the formulae (II), (III), (IV), (V) and (VI) compared to conventional catalysts such as TEGOAMIN® 33, which may be a prerequisite in the application for production of flexible slabstock foams.

Example 4

Production of HR Foams (Block/Molded)

For the performance testing of the inventive nitrogen compounds, the foam formulation specified in Table 13 was used.

TABLE 13

Formulation 4 for cold-cure flexible foam applications (HR block/molded)

| Formulation 4 | Parts by mass (pphp) |
| --- | --- |
| Polyol 1 [1] | 70.0 parts |
| Polyol 2 [2] | 30.0 parts |
| Water | 3.70 parts |
| Glycerol | 0.50 parts |
| Diethanolamine (DEOA) | 1.00 parts |
| Amine | 0.25 parts |
| TEGOSTAB ® B 8716 LF2 [3] | 1.00 parts |
| Desmodur ® T 80 [4] | 44.0 parts |

[1] Polyol 1: sorbitol/glycerol-based polyether polyol having an OH number of 32 mg KOH/g.
[2] Polyol 2: glycerol-based polyether polyol, containing 43% solids (SAN), having an OH number of 20 mg KOH/g.
[3] Formulation of organomodified polysiloxanes.
[4] Tolylene diisocyanate T 80 (80% 2,4 isomer, 20% 2,6 isomer) from Bayer, 3 mPa · s, 48% NCO, functionality 2.

The same foaming methods were employed here as for the conventional flexible polyurethane foam in Examples 2 and 3.

In the foaming operation, 500 g of polyol were used; the other formulation constituents were adjusted correspondingly. In this context, for example, 1.00 part of a component means 1.00 g of a substance per 100 g of polyol.

For the foaming operation, polyol, water, amine and silicone stabilizer were mixed well with stirring. After the isocyanate had been added, the mixture was stirred with a stirrer at 3000 rpm for 4 s and the mixture was cast in a paper-lined wooden box (base area 27 cm×27 cm and height 27 cm). The result was a foam, which was subjected to the performance tests described hereinafter.

The results of the assessment of the catalytic properties of the inventive nitrogen compounds of the formulae (III), (IV) and (V) and the physical properties of the resulting foams are compiled in Table 14. Comparative catalysts used according to the prior art were triethylenediamine, 33% by weight solution in dipropylene glycol (TEGOAMIN® 33, available from Evonik Industries), 1,1'-{[3-(dimethylamino)propyl]imino}bis-2-propanol (TEGOAMIN® ZE 1, available from Evonik Industries), N,N-dimethylethanolamine (TEGOAMIN® DMEA, available from Evonik Industries). 0.25 pphp (=parts by weight based on 100 parts by weight of polyol) of amine was used in each case.

TABLE 14

Results of the foaming operations on formulation 4 (Table 13)

| Amine | Gel time [s] | Rise time [s] | Height [cm] | Fall-back [cm] | Cell count[1] [cm$^{-1}$] |
| --- | --- | --- | --- | --- | --- |
| TEGOAMIN ® 33 | 85 | 151 | 31.2 | 0.4 | 10.5 |
| TEGOAMIN ® ZE 1 | 131 | 215 | 30.4 | −0.1 | 9.0 |
| TEGOAMIN ® DMEA | 148 | 265 | 26.6 | 0.0 | collapse |
| FORMULA (IIa) | 137 | 235 | 29.4 | 0.5 | 9.0 |
| FORMULA (IIIa) | 141 | 243 | 29.0 | 0.0 | 9.0 |
| FORMULA (IIIb) | 155 | 273 | 26.5 | 0.0 | 9.0 |
| FORMULA (IVa) | 153 | 263 | 26.8 | 0.1 | 9.0 |
| FORMULA (Va) | 151 | 275 | 27.1 | 0.1 | 9.0 |
| FORMULA (VIa) | 78 | 157 | 32.1 | 0.6 | 10.0 |

[1] Cell count = number of cells per cm [cm$^{-1}$].

As can be inferred from Table 14, the inventive nitrogen compounds of the formulae (II), (III), (IV), (V) and (VI) in this cold-cure foam formulation show a moderate catalytic activity and selectivity, in some cases comparable to TEGOAMIN® ZE 1 and TEGOAMIN® DMEA. The compound of the formula (VIa) again has a high activity in the range of TEGOAMIN 33, but slight selectivity for the blowing reaction can again be observed.

The invention claimed is:

1. A process for making a polyurethane comprising (1) mixing in a reaction mixture of a polyisocyanate and a polyol a proportion by mass of from 0.01 to 20 parts (pphp), based on 100 parts (pphp) of polyol component of at least one nitrogen compound, or mixtures of the nitrogen compound with corresponding quaternized and/or protonated compounds, wherein this nitrogen compound satisfies formula (VI),

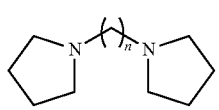

(VI)

with n=2-12 except for 4, and (2) a pyrrolidine group selected from the group consisting of 1-(2-hydroxyethyl)pyrrolidine, 1-(2-chloroethyl)pyrrolidine, and 1-(2-(pyrrolidin-1-yl)propoxy)propan-2-ol.

2. The process according to claim 1, wherein the nitrogen compound of one of the formulae (VI) with n=2, 3 or 6 is used as catalyst in the production of polyurethanes or polyurethane foams.

3. The process according to claim 1, wherein, in the production of the polyurethane or a polyurethane foam, a composition includes at least one nitrogen compound of the formula (VI) with n=6.

4. The process according to claim 1, wherein the at least one nitrogen compound of the formula (VI), is used in combination with at least one solvent, where the mass ratio of the total amount of catalyst used, comprising all the catalytically active compounds of the formula (VI) and not of the formula (VI), to solvent is from 100:1 to 1:4.

5. A polyurethane foam obtained through the method according to claim 1, wherein a finished polyurethane foam is a rigid polyurethane foam, a flexible polyurethane foam, a viscoelastic foam, a cold-cure foam (also called high-resilience (HR) foam), a semirigid polyurethane foam, a thermoformable polyurethane foam or an integral foam.

6. An article comprising the polyurethane foam according to claim 4 wherein the article is selected from the group consisting of refrigerator insulation, insulation panel, sandwich element, pipe insulation, spray foam, 1- and 1.5-pack canned foam, imitation wood, modelling foam, floral foam, packaging foam, mattress, furniture cushion, moldable foam for furniture, pillows, rebonded foam, sponge foam, automobile seat cushion, headrest, dashboard, automobile interior, automobile roof liner, sound absorption material, steering wheel, shoe sole, carpet backing foam, filter foam, sealing foam, sealant and adhesive.

7. A process for making a polyurethane comprising (1) mixing in a reaction mixture of a polyisocyanate and a polyol a proportion by mass of from 0.01 to 20 parts (pphp), based on 100 parts (pphp) of polyol component, of at least one nitrogen compound, or mixtures of the nitrogen compound with corresponding quaternized and/or protonated compounds, wherein this nitrogen compound satisfies formula (VI),

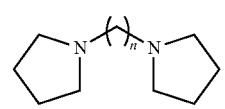

(VI)

with n=2-12 except for 4, and
(2) a pyrrolidine group and diethylene glycol, wherein the pyrrolidine group is a reaction product of pyrrolidine with alkyl halides, a reaction product of pyrrolidine with bischloroalkyl ethers, a reaction product of pyrrolidine with epoxides or epoxide-bearing compounds, or a reaction product of pyrrolidine with alcohols and/or polyols.

8. The process according to claim 7, wherein the pyrrolidine group is selected from the group consisting of 1-(2-hydroxyethyl)pyrrolidine, 1-(2-chloroethyl)pyrrolidine, and 1-(2-(pyrrolidin-1-yl)propoxy)propan-2-ol.

9. The process according to claim 7, wherein the nitrogen compound of one of the formulae (VI) with n=2, 3 or 6 is used as catalyst in the production of polyurethanes or polyurethane foams.

10. The process according to claim 7, wherein, in the production of the polyurethane or a polyurethane foam, a composition includes at least one nitrogen compound of the formula (VI) with n=6.

11. The process according to claim 7, wherein the at least one nitrogen compound of the formula (VI), is used in combination with at least one solvent, where the mass ratio of the total amount of catalyst used, comprising all the catalytically active compounds of the formula (VI) and not of the formula (VI), to solvent is from 100:1 to 1:4.

12. A polyurethane foam obtained through the method according to claim 7, wherein a finished polyurethane foam is a rigid polyurethane foam, a flexible polyurethane foam, a viscoelastic foam, a cold-cure foam (also called high-resilience (HR) foam), a semirigid polyurethane foam, a thermoformable polyurethane foam or an integral foam.

13. An article comprising the polyurethane foam according to claim 12 wherein the article is selected from the group consisting of refrigerator insulation, insulation panel, sandwich element, pipe insulation, spray foam, 1- and 1.5-pack canned foam, imitation wood, modelling foam, floral foam, packaging foam, mattress, furniture cushion, moldable foam for furniture, pillows, rebonded foam, sponge foam, automobile seat cushion, headrest, dashboard, automobile interior, automobile roof liner, sound absorption material, steering wheel, shoe sole, carpet backing foam, filter foam, sealing foam, sealant and adhesive.

* * * * *